(12) United States Patent
King et al.

(10) Patent No.: US 10,557,086 B2
(45) Date of Patent: *Feb. 11, 2020

(54) RESVERATROL-BASED FLAME RETARDANT MATERIALS

(71) Applicant: International Business Machines Corporation, Armonk, NY (US)

(72) Inventors: Scott B. King, Rochester, MN (US); Brandon M. Kobilka, Tucson, AZ (US); Joseph Kuczynski, North Port, FL (US); Jason T. Wertz, Pleasant Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 115 days.

This patent is subject to a terminal disclaimer.

(21) Appl. No.: 15/810,934

(22) Filed: Nov. 13, 2017

(65) Prior Publication Data

US 2018/0346816 A1 Dec. 6, 2018

Related U.S. Application Data

(63) Continuation of application No. 15/609,218, filed on May 31, 2017, now Pat. No. 10,138,423.

(51) Int. Cl.
*C09K 21/12* (2006.01)
*C08F 30/02* (2006.01)
(Continued)

(52) U.S. Cl.
CPC ............... *C09K 21/12* (2013.01); *C07F 9/12* (2013.01); *C07F 9/145* (2013.01); *C07F 9/1406* (2013.01); *C07F 9/4084* (2013.01); *C07F 9/65502* (2013.01); *C07F 9/65515* (2013.01); *C08F 30/02* (2013.01); *C08F 130/02* (2013.01); *C08F 230/02* (2013.01); *C08G 59/02* (2013.01);
(Continued)

(58) Field of Classification Search
CPC .......... C09K 1/12; C08F 30/02; C08F 130/02; C08F 230/02; C08G 59/304; C08G 59/04; C08G 59/02; C08G 59/3272; C08G 59/30; C08G 63/08; C08G 63/12; C08G 63/13; C08G 63/692; C08G 63/6928; C08G 69/02; C08G 69/26; C08G 73/02; C08G 79/02; C08G 79/04; C08G 79/06
See application file for complete search history.

(56) References Cited

U.S. PATENT DOCUMENTS 7,705,188 B2 4/2010 Pettit et al.
8,084,496 B2 12/2011 Maes et al.
8,465,973 B2 6/2013 Declercq et al.

FOREIGN PATENT DOCUMENTS

CN 101691384 A 4/2010
WO WO-2006/029483 A1 3/2006

OTHER PUBLICATIONS

U.S. Appl. No. 15/609,218, to Scott B. King et al., entitled, *Resveratrol-Based Flame Retardant Materials*, assigned to International Business Machines Corporation, 59 pages, filed May 31, 2017.

(Continued)

*Primary Examiner* — Ling Siu Choi
*Assistant Examiner* — David L Miller
(74) *Attorney, Agent, or Firm* — Robert J. Shatto

(57) ABSTRACT

A process of forming a resveratrol-based flame retardant small molecule with a phosphonate/phosphinate molecule that includes a chloride group and a terminal functional group.

5 Claims, 22 Drawing Sheets

(51) Int. Cl.
*C08G 59/02* (2006.01)
*C07F 9/40* (2006.01)
*C08K 5/5333* (2006.01)
*C09K 21/14* (2006.01)
*C07F 9/12* (2006.01)
*C08F 230/02* (2006.01)
*C07F 9/145* (2006.01)
*C08K 5/5337* (2006.01)
*C08F 130/02* (2006.01)
*C08K 5/5373* (2006.01)
*C08K 5/5353* (2006.01)
*C08K 5/5357* (2006.01)
*C08G 59/30* (2006.01)
*C08G 79/02* (2016.01)
*C08G 59/04* (2006.01)
*C08G 73/02* (2006.01)
*C08G 69/02* (2006.01)
*C08G 63/08* (2006.01)
*C07F 9/14* (2006.01)
*C07F 9/655* (2006.01)
*C08K 5/52* (2006.01)
*C08G 59/32* (2006.01)
*C08G 79/06* (2006.01)
*C08G 69/26* (2006.01)
*C08G 63/13* (2006.01)
*C08G 63/692* (2006.01)
*C08G 63/12* (2006.01)

(52) U.S. Cl.
CPC ........... *C08G 59/04* (2013.01); *C08G 59/304* (2013.01); *C08G 63/08* (2013.01); *C08G 69/02* (2013.01); *C08G 73/02* (2013.01); *C08G 79/02* (2013.01); *C08K 5/52* (2013.01); *C08K 5/5333* (2013.01); *C08K 5/5337* (2013.01); *C08K 5/5353* (2013.01); *C08K 5/5357* (2013.01); *C08K 5/5373* (2013.01); *C09K 21/14* (2013.01); *C08G 59/3272* (2013.01); *C08G 63/12* (2013.01); *C08G 63/13* (2013.01); *C08G 63/692* (2013.01); *C08G 63/6928* (2013.01); *C08G 69/26* (2013.01); *C08G 79/06* (2013.01)

(56) References Cited

OTHER PUBLICATIONS

Appendix P; List of IBM Patent or Applications Treated as Related, Nov. 10, 2017, 2 pages.
U.S. Appl. No. 16/111,683, to Scott B. King et al., entitled, *Resveratrol-Based Flame Retardant Materials*, assigned to International Business Machines Corporation, 59 pages, filed Aug. 24, 2018.
Appendix P; List of IBM Patent or Applications Treated as Related, Aug. 30, 2018, 2 pages.

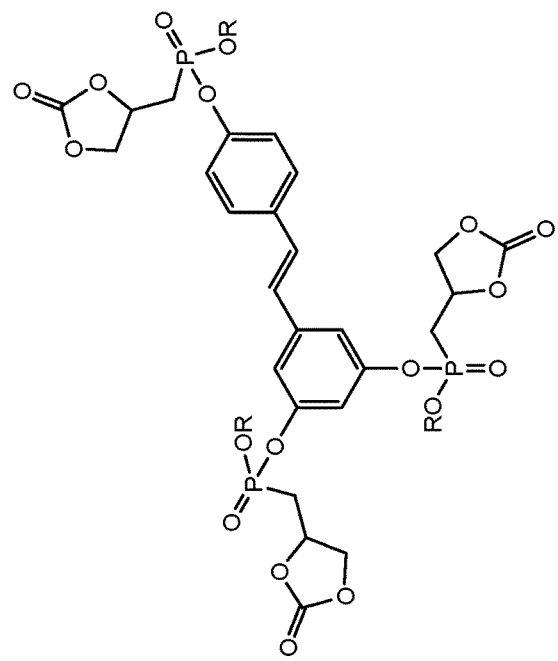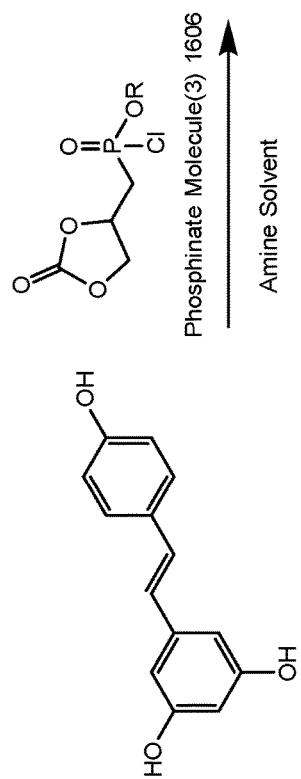
FIG. 16

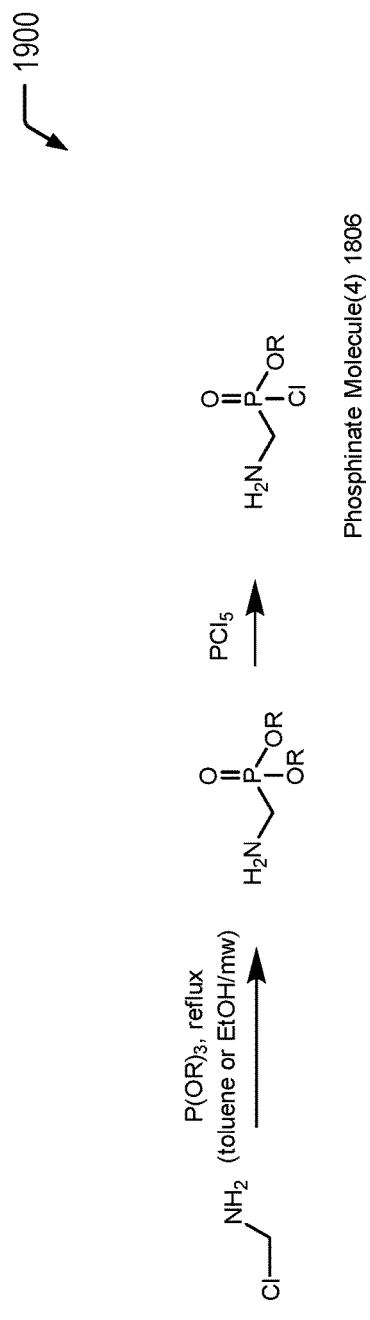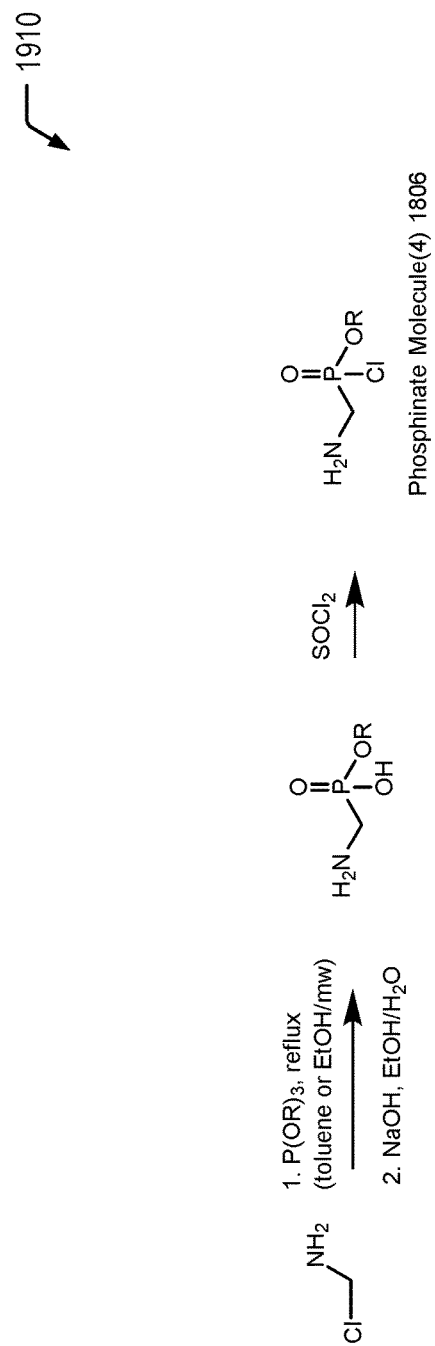

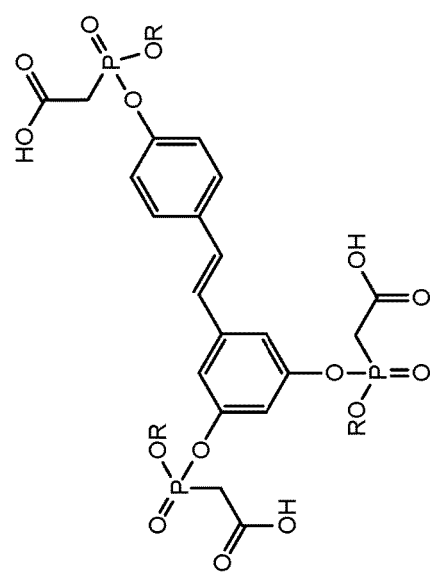
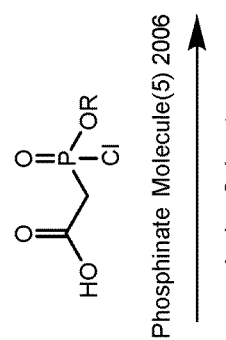
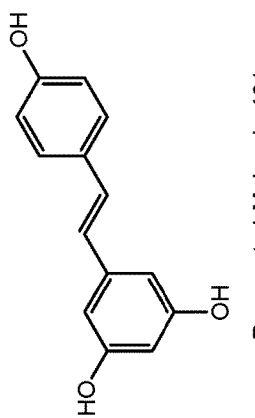
FIG. 20

RESVERATROL-BASED FLAME RETARDANT MATERIALS

CROSS-REFERENCE TO RELATED APPLICATION

This application is a continuation application of U.S. patent application Ser. No. 15/609,218, filed May 31, 2017.

BACKGROUND

Plastics are typically derived from a finite and dwindling supply of petrochemicals, resulting in price fluctuations and supply chain instability. Replacing non-renewable petroleum-based polymers with polymers derived from renewable resources may be desirable. However, there may be limited alternatives to petroleum-based polymers in certain contexts. To illustrate, particular plastics performance standards may be specified by a standards body or by a regulatory agency. In some cases, alternatives to petroleum-based polymers may be limited as a result of challenges associated with satisfying particular plastics performance standards.

SUMMARY

According to an embodiment, a process of forming a resveratrol-based flame retardant small molecule is disclosed. The process includes chemically reacting a resveratrol molecule with a phosphonate molecule that includes a chloride group and a terminal functional group.

According to another embodiment, a resveratrol-based flame retardant small molecule is disclosed having the following formula:

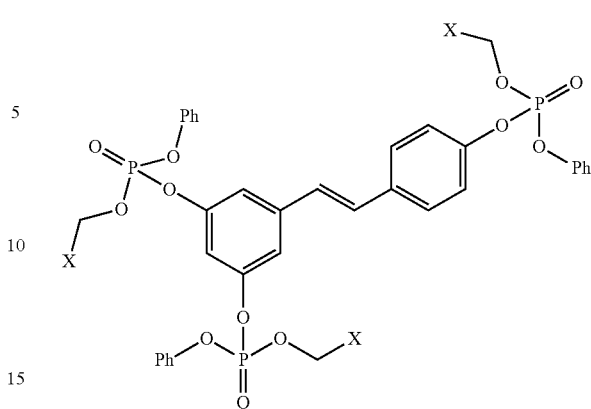

In the above formula, X includes a terminal functional group selected from the group consisting of: an allyl group; an epoxide group; a lactone group; an amine group; and a carboxyl group.

According to another embodiment, a process of forming a resveratrol-based flame retardant small molecule is disclosed. The process includes chemically reacting a resveratrol molecule with a phosphinate molecule that includes a chloride group and a terminal functional group.

According to yet another embodiment, a resveratrol-based flame retardant small molecule is disclosed having the following formula:

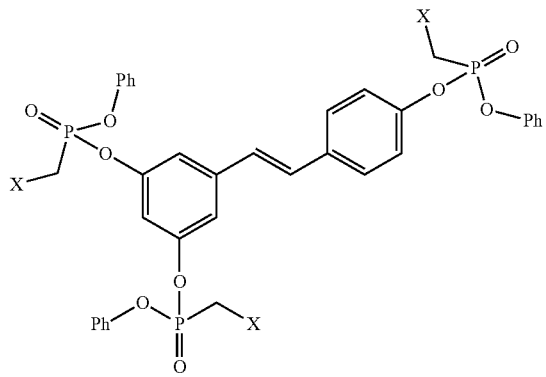

In the above formula, X includes a terminal reactive group selected from the group consisting of: an allyl group; an epoxide group; a lactone group; an amine group; and a carboxyl group.

The foregoing and other objects, features, and advantages of the invention will be apparent from the following more particular descriptions of exemplary embodiments of the invention as illustrated in the accompanying drawings wherein like reference numbers generally represent like parts of exemplary embodiments of the invention.

BRIEF DESCRIPTION OF THE DRAWINGS

FIG. 16 is a chemical reaction diagram illustrating a process of forming an eighth resveratrol-based flame retardant small molecule, according to one embodiment.

FIGS. 19A and 19B are chemical reaction diagrams showing alternative embodiments of processes of forming a fourth phosphinate molecule for forming the ninth resveratrol-based flame retardant small molecule depicted in FIG. 18.

FIG. 20 is a chemical reaction diagram illustrating a process of forming a tenth resveratrol-based flame retardant small molecule, according to one embodiment.

DETAILED DESCRIPTION

The present disclosure describes flame retardant materials derived from the biorenewable molecule resveratrol (3,5,4'-trihydroxy-trans-stilbene) and methods of forming the flame retardant materials from the biorenewable molecule resveratrol. The biorenewable molecule resveratrol may be extracted from plants, where it is produced in response to injury or when the plant is under attack by pathogens such as bacteria or fungi.

In some embodiments of the present disclosure, a resveratrol molecule may be chemically reacted with a phosphorus-containing molecule to form a resveratrol-based molecule having one or more phosphorus-based flame retardant moieties. In the present disclosure, the phosphorus-containing molecule includes a phosphoryl group (i.e., a phosphorus-oxygen double bond), a chloride group, and an additional reactive functional group (e.g., an allyl group, an epoxide group, a lactone group, an amine group, or a carboxyl group). The resveratrol-based molecule having the phosphorus-based flame retardant moiety (or moieities) is also referred to herein as a resveratrol-based flame retardant small molecule. In some cases, the resveratrol-based flame retardant small molecules of the present disclosure may be added to a variety of polymeric materials to not only impart flame retardancy characteristics to the polymeric materials but also increase the biorenewable content of the polymeric materials.

In some embodiments of the present disclosure, the additional reactive functional group may enable the resveratrol-based flame retardant small molecule to be utilized as a monomer to form a resveratrol-based polymer having phosphorus-based flame retardant moieties. The resveratrol-based polymers having the phosphorus-based flame retardant moieties are also referred to herein as resveratrol-based flame retardant polymers. In some cases, the resveratrol-based flame retardant polymers of the present disclosure may be utilized as stand-alone polymers. In other cases, the resveratrol-based flame retardant polymers of the present disclosure may be blended with other polymeric materials (e.g., petroleum-based polymers) to form a polymeric blend. In such cases, the resveratrol-based flame retardant polymers not only impart flame retardancy characteristics to the polymeric blend but also increase the biorenewable content of the polymeric blend.

Figure 1:
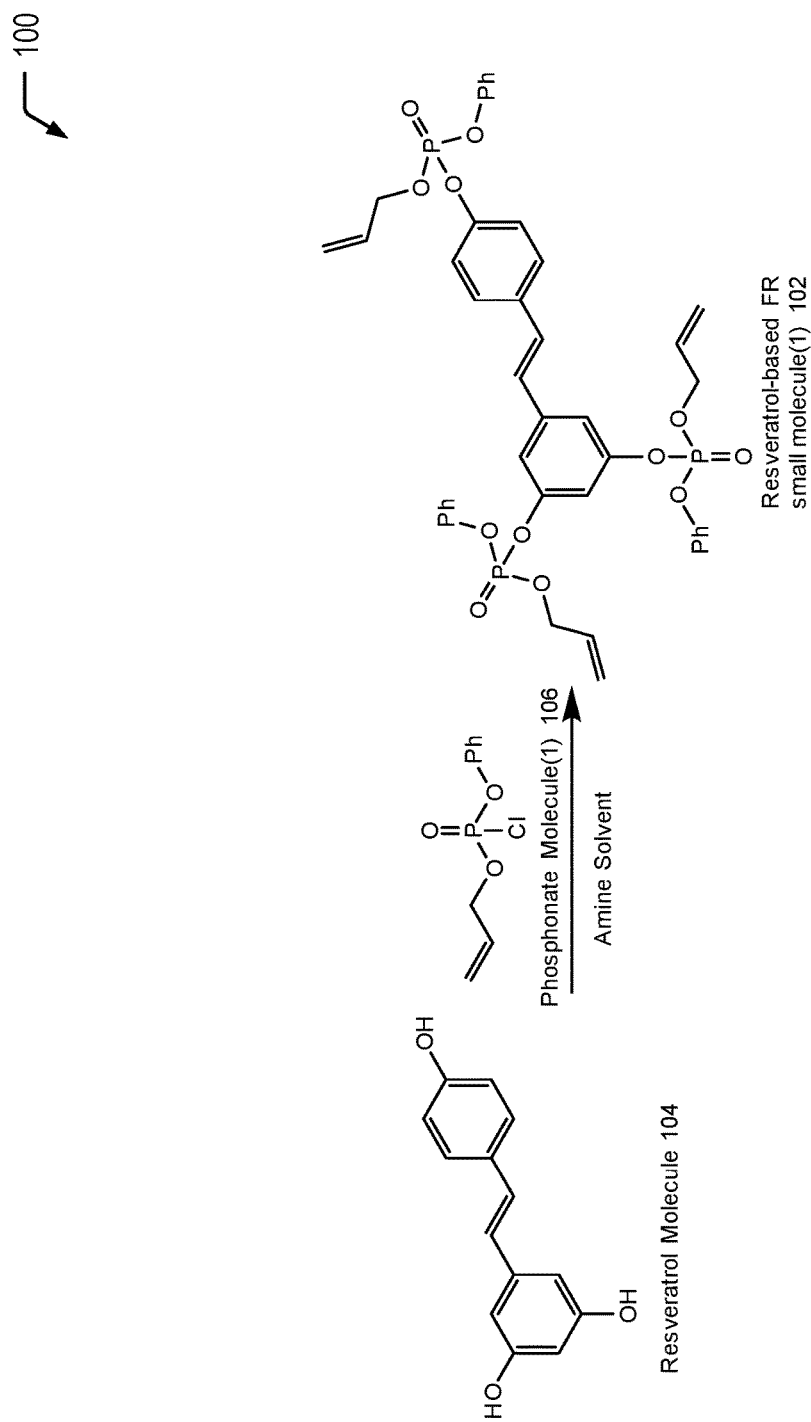
FIG. 1 is a chemical reaction diagram illustrating a process of forming a first resveratrol-based flame retardant small molecule, according to one embodiment.

Referring to FIG. 1, a chemical reaction diagram 100 illustrates a process of forming a first resveratrol-based flame retardant (FR) small molecule 102, according to one embodiment. In the particular embodiment depicted in FIG. 1, the first resveratrol-based FR small molecule 102 is formed via a chemical reaction of a resveratrol molecule 104 (which may be derived from plants) and a first phosphonate molecule 106. As further described herein, the first phosphonate molecule 106 depicted in FIG. 1 may be synthesized according to one of the processes described herein with respect to FIGS. 2A and 2B.

The first phosphonate molecule 106 depicted in FIG. 1 represents an example of a phosphorus-containing molecule in which the additional reactive group corresponds to an allyl group. FIG. 1 illustrates that a chloride group of the first phosphonate molecule 106 reacts with a hydroxyl group of the resveratrol molecule 104 to form a phosphorus-oxygen single bond between the phosphorus atom of the phosphoryl group and the oxygen atom of the hydroxyl group. As a prophetic example, the resveratrol molecule 104 may be chemically reacted with the first phosphonate molecule 106 in an amine solvent to yield the first resveratrol-based FR small molecule 102.

In the embodiment depicted in FIG. 1, each hydroxyl group of the three hydroxyl groups of the resveratrol molecule 104 chemically reacts with the chloride group of the first phosphonate molecule 106 to form the first resveratrol-based FR small molecule 102 having three phosphorus-based flame retardant moieties (and three allyl functional groups). It will be appreciated that, in other cases, the reaction stoichiometry may be adjusted to form an alternative resveratrol-based FR small molecule having less than three phosphorus-based flame retardant moieties (and less than three allyl functional groups).

Thus, FIG. 1 illustrates an example of a process of forming a resveratrol-based flame retardant small molecule that includes an allyl functional group via a chemical reaction of a resveratrol molecule and a phosphonate molecule that includes the allyl functional group.

Figure 2A:
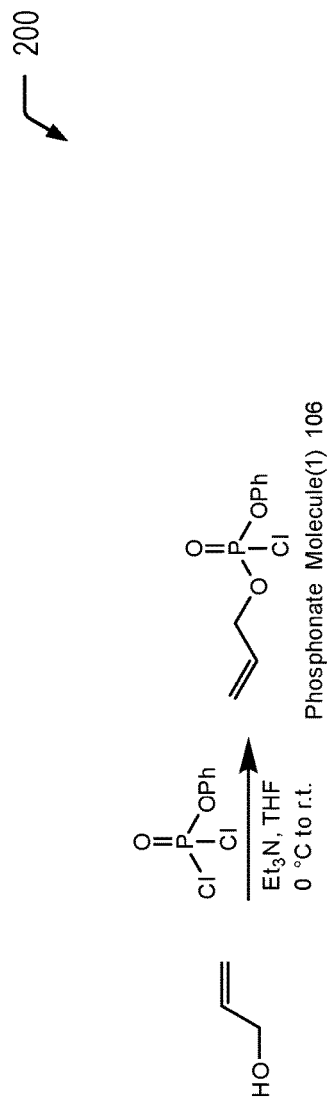
FIGS. 2A and 2B are chemical reaction diagrams showing alternative embodiments of processes of forming a first phosphonate molecule for forming the first resveratrol-based flame retardant small molecule depicted in FIG. 1.
Figure 2B:
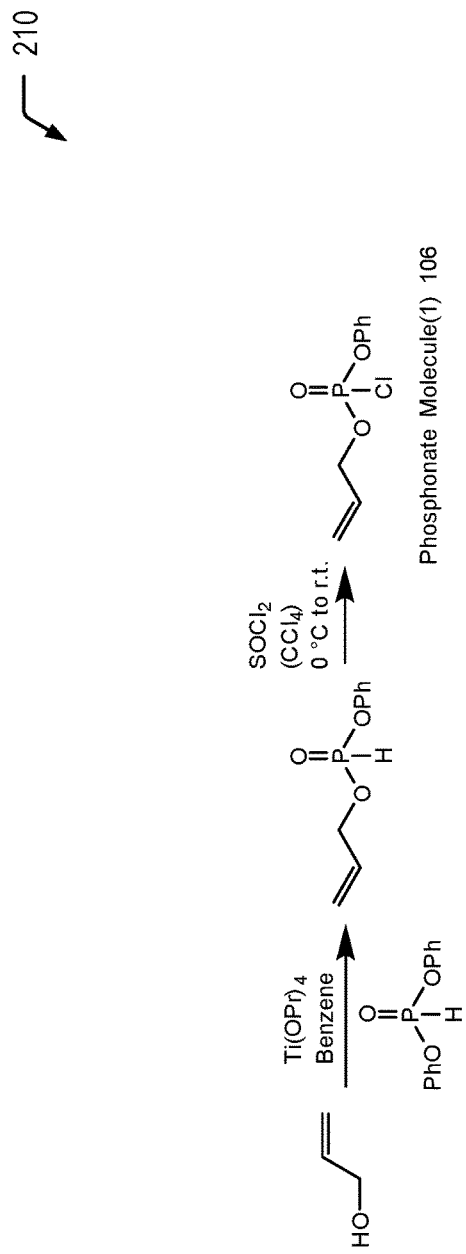

FIGS. 2A and 2B are chemical reaction diagrams showing alternative embodiments of processes of forming the first phosphonate molecule 106 depicted in FIG. 1. The first phosphonate molecule 106 depicted in FIGS. 2A and 2B represents an example of a phosphonate molecule that is functionalized with a chloride group for bonding with a hydroxyl group of a resveratrol molecule and an allyl functional group that may be utilized to form a resveratrol-derived flame retardant polymer, as described further herein with respect to FIG. 11.

Referring to FIG. 2A, a first chemical reaction diagram 200 illustrates a first embodiment of a process of forming the first phosphonate molecule 106. In FIG. 2A, the first phosphonate molecule 106 is formed via a one-step process via reaction of allyl alcohol with phenyl dichlorophosphate via careful addition and stoichiometric control.

As a prophetic example, to a stirred solution that includes allyl alcohol (1.0 eq.) and triethylamine (2.0 eq.) in anhydrous THF, phenyl dichlorophosphate (1.3 eq.) may be added dropwise at 0° C., and the reaction mixture may be stirred at ambient temperature for 2 hours or the reaction mixture may be heated up to reflux (60-65° C.) for an extended reaction time (4 hours). The reaction mixture may be cooled to ambient temperature and filtered to remove the triethylamine hydrochloride salt. The solvents of the filtrate may be removed in vacuo, and the product may be purified by fractional distillation.

Referring to FIG. 2B, a second chemical reaction diagram 210 illustrates an alternative embodiment of a process of forming the first phosphonate molecule 106. The first chemical reaction depicted in FIG. 2B illustrates that allyl alcohol may be reacted with titanium (IV) isopropoxide and phosphonic acid diphenyl ester via a pseudo-esterification to form an intermediate molecule. The second chemical reaction depicted in FIG. 2B illustrates that the intermediate molecule may be reacted with thionyl chloride to form the first phosphonate molecule 106.

As a prophetic example, diaryl phosphite (5.5 mmol) may be added to a solution of titanium (IV) isopropoxide, $Ti(OPr)_4$ (11 mmol), in allyl alcohol (excess). This solution may be diluted with benzene. The reaction mixture may be heated to 40° C. until completion. The mixture may be poured into water, extracted with $CH_2Cl_2$ (3×), dried over $MgSO_4$, and solvent and volatile components may be removed in vacuo. The products may be purified by fractional distillation or recrystallization. The product from the first step (1.0 eq.), in dry acetonitrile (MeCN), toluene, or dichloromethane (DCM), may be added to a solution of trichloroisocyanuric acid (0.33 eq.), N-chlorosuccinimide (1.0 eq.), or tert-butyl hypochlorite (1.0 eq.) in the same solvent at room temperature, under an $N_2$ atmosphere. Upon formation of a precipitate, the reaction may be stirred at room temperature for an additional 2 hours. Upon completion of the reaction, as determined by $^{31}P$ NMR, the reaction mixture may be passed through a 0.45 μm Whatman syringe filter and concentrated under vacuum. Next, thionyl chloride ($SOCl_2$) may be dissolved in a suitable solvent, such as carbon tetrachloride ($CCl_4$), and the chemical reaction may be performed from 0° C. to room temperature.

Thus, FIGS. 2A and 2B illustrate alternative processes of forming a phosphonate molecule that is functionalized with a chloride group for bonding with a hydroxyl group of a resveratrol molecule and an allyl functional group that may be utilized to form a resveratrol-based flame retardant polymer. While FIGS. 2A and 2B illustrate an example in which the phosphonate molecule includes a phenyl group, it will be appreciated that the phenyl group may be substituted by ethyl, methyl, propyl, or isopropyl groups, among other alternatives.

Figure 3:
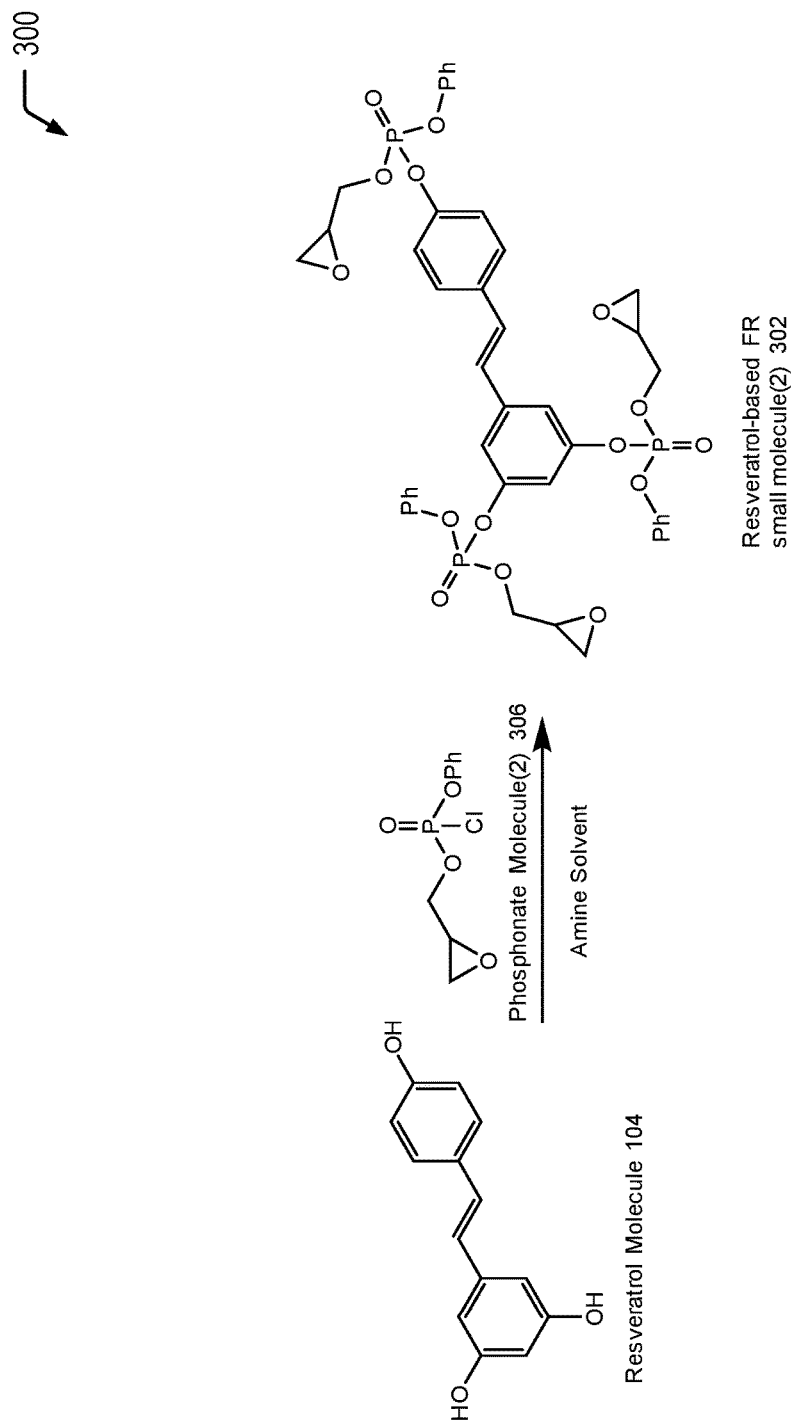
FIG. 3 is a chemical reaction diagram illustrating a process of forming a second resveratrol-based flame retardant small molecule, according to one embodiment.

Referring to FIG. 3, a chemical reaction diagram 300 illustrates a process of forming a second resveratrol-based FR small molecule 302, according to one embodiment. In the particular embodiment depicted in FIG. 3, the second resveratrol-based FR small molecule 302 is formed via a chemical reaction of the resveratrol molecule 104 and a second phosphonate molecule 306. As further described herein, the second phosphonate molecule 306 depicted in FIG. 3 may be synthesized according to one of the processes described herein with respect to FIGS. 4A and 4B.

The second phosphonate molecule 306 depicted in FIG. 3 represents an example of a phosphorus-containing molecule in which the additional reactive group corresponds to an epoxide group. FIG. 3 illustrates that a chloride group of the second phosphonate molecule 306 reacts with a hydroxyl group of the resveratrol molecule 104 to form a phosphorus-oxygen single bond between the phosphorus atom of the phosphoryl group and the oxygen atom of the hydroxyl group. As a prophetic example, the resveratrol molecule 104 may be chemically reacted with the second phosphonate molecule 306 in an amine solvent to yield the second resveratrol-based FR small molecule 302.

In the embodiment depicted in FIG. 3, each hydroxyl group of the three hydroxyl groups of the resveratrol molecule 104 chemically reacts with the chloride group of the second phosphonate molecule 306 to form the second resveratrol-based FR small molecule 302 having three phosphorus-based flame retardant moieties (and three epoxide functional groups). It will be appreciated that, in other cases, the reaction stoichiometry may be adjusted to form an alternative resveratrol-based FR small molecule having less than three phosphorus-based flame retardant moieties (and less than three epoxide functional groups).

Thus, FIG. 3 illustrates an example of a process of forming a resveratrol-derived flame retardant small molecule that includes an epoxide functional group via a chemical reaction of a resveratrol molecule and a phosphonate molecule that includes the epoxide functional group.

Figure 4A:
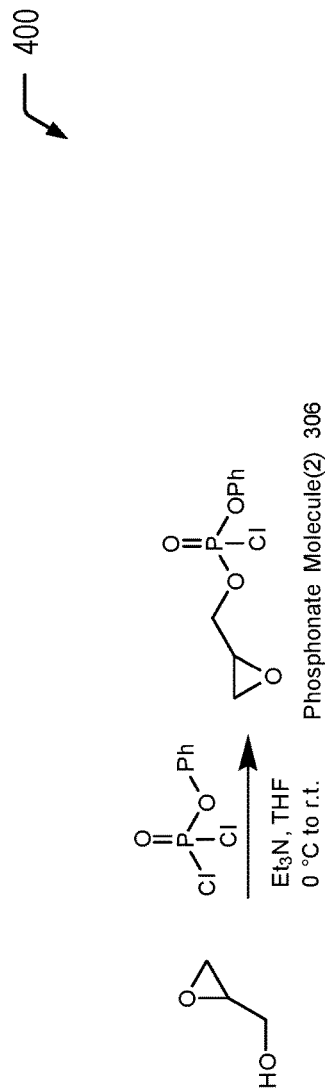
FIGS. 4A and 4B are chemical reaction diagrams showing alternative embodiments of processes of forming a second phosphonate molecule for forming the second resveratrol-based flame retardant small molecule depicted in FIG. 3.
Figure 4B:
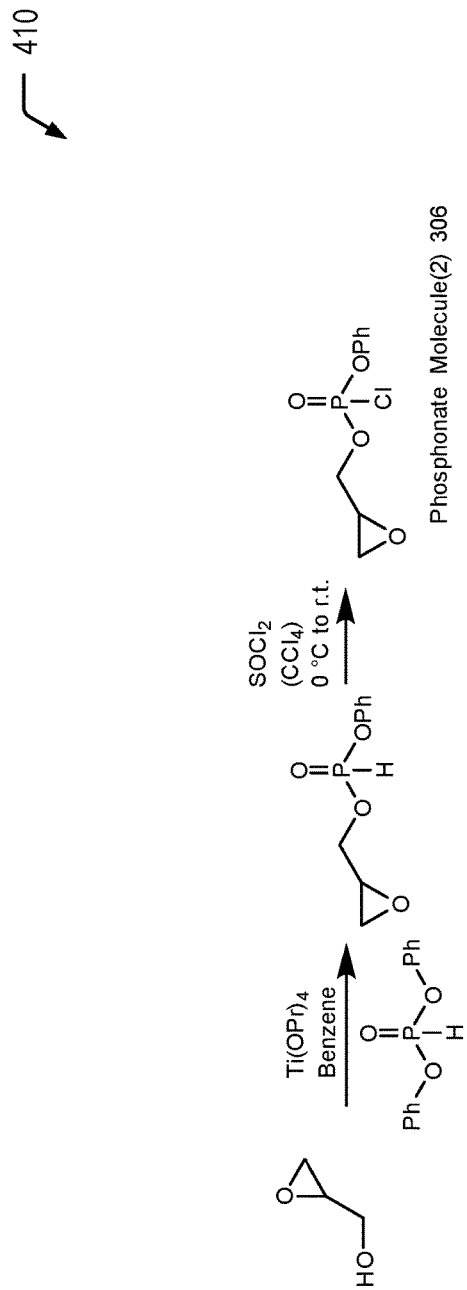

FIGS. 4A and 4B are chemical reaction diagrams showing alternative embodiments of processes of forming the second phosphonate molecule 306 depicted in FIG. 3. The second phosphonate molecule 306 depicted in FIGS. 4A and 4B represents an example of a phosphonate molecule that is functionalized with a chloride group for bonding with a hydroxyl group of a resveratrol molecule and an epoxide functional group that may be utilized to form a resveratrol-based flame retardant polymer, as described further herein with respect to FIG. 11.

Referring to FIG. 4A, a first chemical reaction diagram 400 illustrates a first embodiment of a process of forming the second phosphonate molecule 306. In FIG. 4A, the second phosphonate molecule 306 is formed via a one-step process via reaction of glycidol with phenyl dichlorophosphate via careful addition and stoichiometric control.

As a prophetic example, to a stirred solution that includes glycidol (1.0 eq.) and triethylamine (2.0 eq.) in anhydrous THF, phenyl dichlorophosphate (1.3 eq.) may be added dropwise at 0° C., and the reaction mixture may be stirred at ambient temperature for 2 hours or the reaction mixture may be heated up to reflux (60-65° C.) for an extended reaction time (4 hours). The reaction mixture may be cooled to ambient temperature and filtered to remove the triethylamine hydrochloride salt. The solvents of the filtrate may be removed in vacuo, and the product may be purified by fractional distillation.

Referring to FIG. 4B, a second chemical reaction diagram 410 illustrates an alternative embodiment of a process of forming the second phosphonate molecule 306. The first chemical reaction depicted in FIG. 4B illustrates that glycidol may be reacted with titanium (IV) isopropoxide and phosphonic acid diphenyl ester via a pseudo-esterification to form an intermediate molecule. The second chemical reaction depicted in FIG. 4B illustrates that the intermediate molecule may be reacted with thionyl chloride to form the second phosphonate molecule 306.

As a prophetic example, diaryl phosphite (5.5 mmol) may be added to a solution of titanium (IV) isopropoxide, $Ti(OPr)_4$ (11 mmol), in glycidol (excess). This solution may be diluted with benzene. The reaction mixture may be heated to 40° C. until completion. The mixture may be poured into water, extracted with $CH_2Cl_2$ (3×), dried over $MgSO_4$, and solvent and volatile components may be removed in vacuo. The products may be purified by fractional distillation or recrystallization. The product from the first step (1.0 eq.), in dry acetonitrile (MeCN), toluene, or dichloromethane (DCM), may be added to a solution of trichloroisocyanuric acid (0.33 eq.), N-chlorosuccinimide (1.0 eq.), or tert-butyl hypochlorite (1.0 eq.) in the same solvent at room temperature, under an $N_2$ atmosphere. Upon formation of a precipitate, the reaction may be stirred at room temperature for an additional 2 hours. Upon completion of the reaction, as determined by $^{31}P$ NMR, the reaction mixture may be passed through a 0.45 μm Whatman syringe filter and concentrated under vacuum. Next, thionyl chloride ($SOCl_2$) may be dissolved in a suitable solvent, such as carbon tetrachloride ($CCl_4$), and the chemical reaction may be performed from 0° C. to room temperature.

Thus, FIGS. 4A and 4B illustrate alternative processes of forming a phosphonate molecule that is functionalized with a chloride group for bonding with a hydroxyl group of a resveratrol molecule and an epoxide functional group that may be utilized to form a resveratrol-based flame retardant polymer. While FIGS. 4A and 4B illustrate an example in which the phosphonate molecule includes a phenyl group, it will be appreciated that the phenyl group may be substituted by ethyl, methyl, propyl, or isopropyl groups, among other alternatives.

Figure 5:
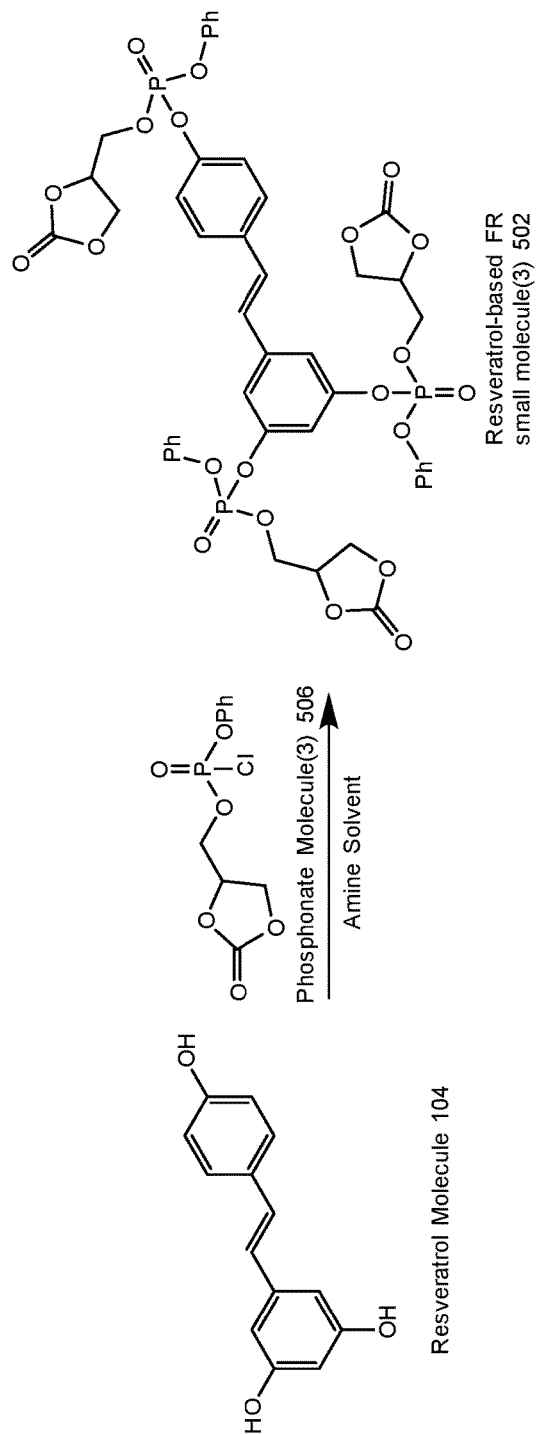
FIG. 5 is a chemical reaction diagram illustrating a process of forming a third resveratrol-based flame retardant small molecule, according to one embodiment.

Referring to FIG. 5, a chemical reaction diagram 500 illustrates a process of forming a third resveratrol-based FR small molecule 502, according to one embodiment. In the particular embodiment depicted in FIG. 5, the third resveratrol-based FR small molecule 502 is formed via a chemical reaction of the resveratrol molecule 104 and a third phosphonate molecule 506. As further described herein, the third phosphonate molecule 506 depicted in FIG. 5 may be synthesized according to one of the processes described herein with respect to FIGS. 6A and 6B.

The third phosphonate molecule 506 depicted in FIG. 5 represents an example of a phosphorus-containing molecule in which the additional reactive group corresponds to a lactone group. FIG. 5 illustrates that a chloride group of the third phosphonate molecule 506 reacts with a hydroxyl group of the resveratrol molecule 104 to form a phosphorus-oxygen single bond between the phosphorus atom of the phosphoryl group and the oxygen atom of the hydroxyl group. As a prophetic example, the resveratrol molecule 104 may be chemically reacted with the third phosphonate molecule 506 in an amine solvent to yield the third resveratrol-based FR small molecule 502.

In the embodiment depicted in FIG. 5, each hydroxyl group of the three hydroxyl groups of the resveratrol molecule 104 chemically reacts with the chloride group of the third phosphonate molecule 506 to form the third resveratrol-based FR small molecule 502 having three phosphorus-based flame retardant moieties (and three lactone functional groups). It will be appreciated that, in other cases, the reaction stoichiometry may be adjusted to form an alternative resveratrol-based FR small molecule having less than three phosphorus-based flame retardant moieties (and less than three lactone functional groups).

Thus, FIG. 5 illustrates an example of a process of forming a resveratrol-based flame retardant small molecule that includes a lactone functional group via a chemical reaction of a resveratrol molecule and a phosphonate molecule that includes the lactone functional group.

Figure 6A:
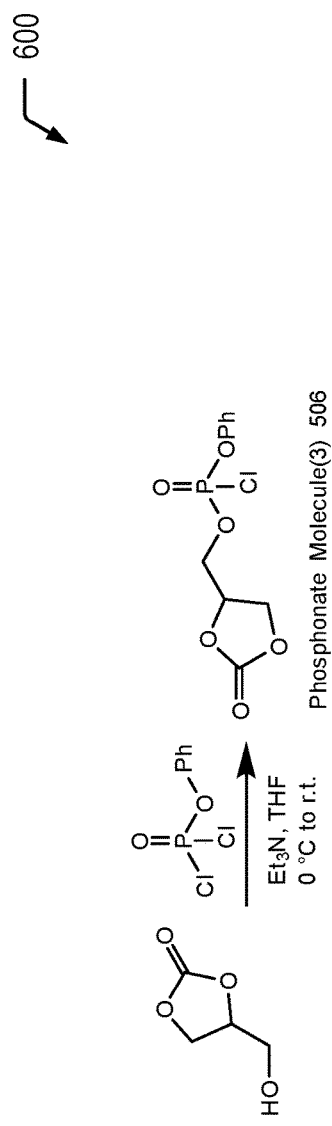
FIGS. 6A and 6B are chemical reaction diagrams showing alternative embodiments of processes of forming a third phosphonate molecule for forming the third resveratrol-based flame retardant small molecule depicted in FIG. 5.
Figure 6B:
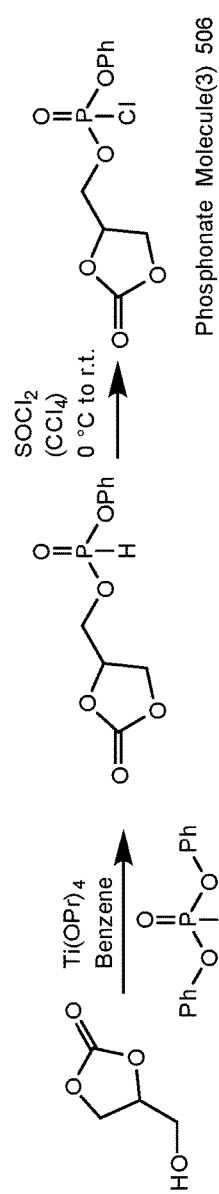

FIGS. 6A and 6B are chemical reaction diagrams showing alternative embodiments of processes of forming the third phosphonate molecule 506 depicted in FIG. 5. The third phosphonate molecule 506 depicted in FIGS. 6A and 6B represents an example of a phosphonate molecule that is functionalized with a chloride group for bonding with a hydroxyl group of a resveratrol molecule and a lactone functional group that may be utilized to form a resveratrol-based flame retardant polymer, as described further herein with respect to FIG. 11.

Referring to FIG. 6A, a first chemical reaction diagram 600 illustrates a first embodiment of a process of forming the third phosphonate molecule 506. In FIG. 6A, the third phosphonate molecule 506 is formed via a one-step process via reaction of 4-Hydroxymethyl-1,3-dioxolan-2-one with phenyl dichlorophosphate via careful addition and stoichiometric control.

As a prophetic example, to a stirred solution that includes 4-Hydroxymethyl-1,3-dioxolan-2-one (1.0 eq.) and triethylamine (2.0 eq.) in anhydrous THF, phenyl dichlorophosphate (1.3 eq.) may be added dropwise at 0° C., and the reaction mixture may be stirred at ambient temperature for 2 hours or the reaction mixture may be heated up to reflux (60-65° C.) for an extended reaction time (4 hours). The reaction mixture may be cooled to ambient temperature and filtered to remove the triethylamine hydrochloride salt. The solvents of the filtrate may be removed in vacuo, and the product may be purified by fractional distillation.

Referring to FIG. 6B, a second chemical reaction diagram 610 illustrates an alternative embodiment of a process of forming the third phosphonate molecule 506. The first chemical reaction depicted in FIG. 6B illustrates that 4-Hydroxymethyl-1,3-dioxolan-2-one may be reacted with titanium (IV) isopropoxide and phosphonic acid diphenyl ester via a pseudo-esterification to form an intermediate molecule. The second chemical reaction depicted in FIG. 6B illustrates that the intermediate molecule may be reacted with thionyl chloride to form the third phosphonate molecule 506.

As a prophetic example, diaryl phosphite (5.5 mmol) may be added to a solution of titanium (IV) isopropoxide, $Ti(OPr)_4$ (11 mmol), in 4-Hydroxymethyl-1,3-dioxolan-2-one (excess). This solution may be diluted with benzene. The reaction mixture may be heated to 40° C. until completion. The mixture may be poured into water, extracted with $CH_2Cl_2$ (3x), dried over $MgSO_4$, and solvent and volatile components may be removed in vacuo. The products may be purified by fractional distillation or recrystallization. The product from the first step (1.0 eq.), in dry acetonitrile (MeCN), toluene, or dichloromethane (DCM), may be added to a solution of trichloroisocyanuric acid (0.33 eq.), N-chlorosuccinimide (1.0 eq.), or tert-butyl hypochlorite (1.0 eq.) in the same solvent at room temperature, under an $N_2$ atmosphere. Upon formation of a precipitate, the reaction may be stirred at room temperature for an additional 2 hours. Upon completion of the reaction, as determined by $^{31}P$ NMR, the reaction mixture may be passed through a 0.45 µm Whatman syringe filter and concentrated under vacuum. Next, thionyl chloride ($SOCl_2$) may be dissolved in a suitable solvent, such as carbon tetrachloride ($CCl_4$), and the chemical reaction may be performed from 0° C. to room temperature.

Thus, FIGS. 6A and 6B illustrate alternative processes of forming a phosphonate molecule that is functionalized with a chloride group for bonding with a hydroxyl group of a resveratrol molecule and a lactone functional group that may be utilized to form a resveratrol-based flame retardant polymer. While FIGS. 6A and 6B illustrate an example in which the phosphonate molecule includes a phenyl group, it will be appreciated that the phenyl group may be substituted by ethyl, methyl, propyl, or isopropyl groups, among other alternatives.

Figure 7:
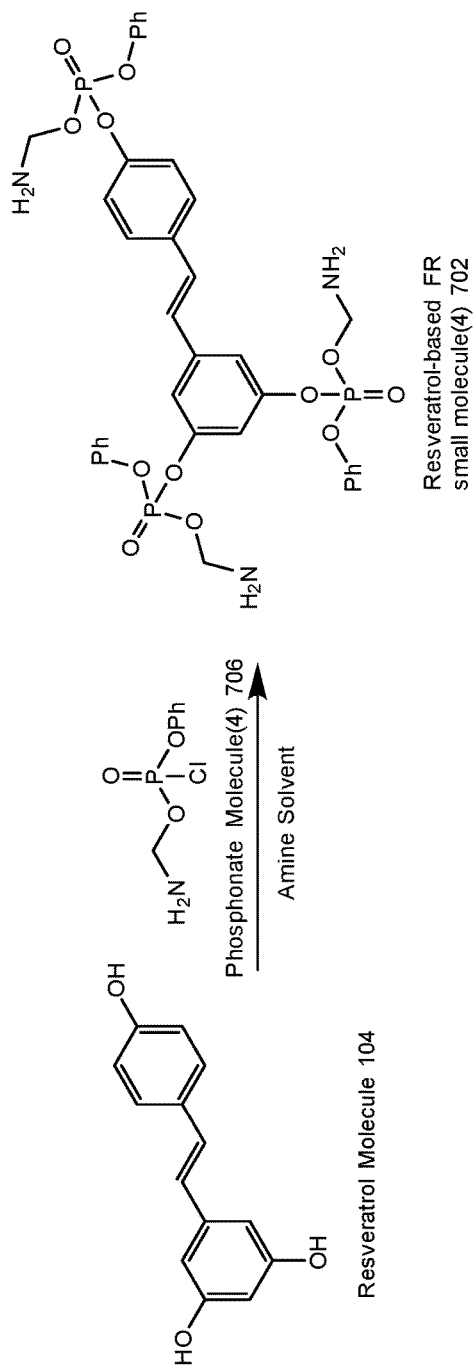
FIG. 7 is a chemical reaction diagram illustrating a process of forming a fourth resveratrol-based flame retardant small molecule, according to one embodiment.

Referring to FIG. 7, a chemical reaction diagram 700 illustrates a process of forming a fourth resveratrol-based FR small molecule 702, according to one embodiment. In the particular embodiment depicted in FIG. 7, the fourth resveratrol-based FR small molecule 702 is formed via a chemical reaction of the resveratrol molecule 104 and a fourth phosphonate molecule 706. As further described herein, the fourth phosphonate molecule 706 depicted in FIG. 7 may be synthesized according to one of the processes described herein with respect to FIGS. 8A and 8B.

The fourth phosphonate molecule 706 depicted in FIG. 7 represents an example of a phosphorus-containing molecule in which the additional reactive group corresponds to an amine group. FIG. 7 illustrates that a chloride group of the fourth phosphonate molecule 706 reacts with a hydroxyl group of the resveratrol molecule 104 to form a phosphorus-oxygen single bond between the phosphorus atom of the phosphoryl group and the oxygen atom of the hydroxyl group. As a prophetic example, the resveratrol molecule 104 may be chemically reacted with the fourth phosphonate molecule 706 in an amine solvent to yield the fourth resveratrol-based FR small molecule 702.

In the embodiment depicted in FIG. 7, each hydroxyl group of the three hydroxyl groups of the resveratrol molecule 104 chemically reacts with the chloride group of the fourth phosphonate molecule 706 to form the fourth resveratrol-based FR small molecule 702 having three phosphorus-based flame retardant moieties (and three amine functional groups). It will be appreciated that, in other cases, the reaction stoichiometry may be adjusted to form an alternative resveratrol-based FR small molecule having less than three phosphorus-based flame retardant moieties (and less than three amine functional groups).

Thus, FIG. 7 illustrates an example of a process of forming a resveratrol-based flame retardant small molecule that includes an amine functional group via a chemical reaction of a resveratrol molecule and a phosphonate molecule that includes the amine functional group.

Figure 8A:
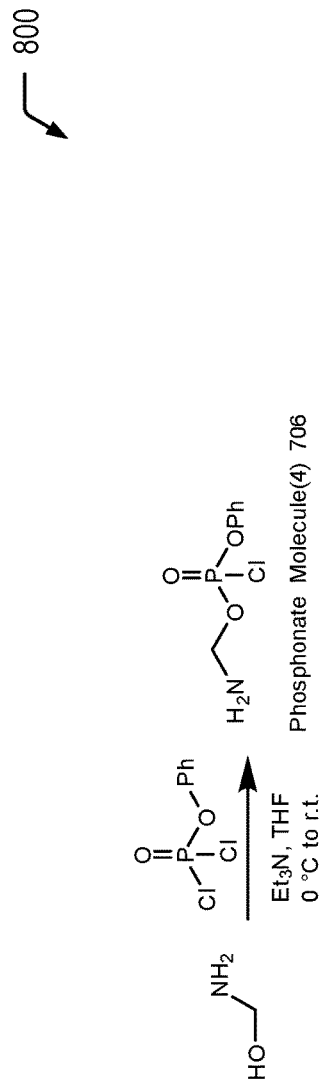
FIGS. 8A and 8B are chemical reaction diagrams showing alternative embodiments of processes of forming a fourth phosphonate molecule for forming the fourth resveratrol-based flame retardant small molecule depicted in FIG. 7.
Figure 8B:
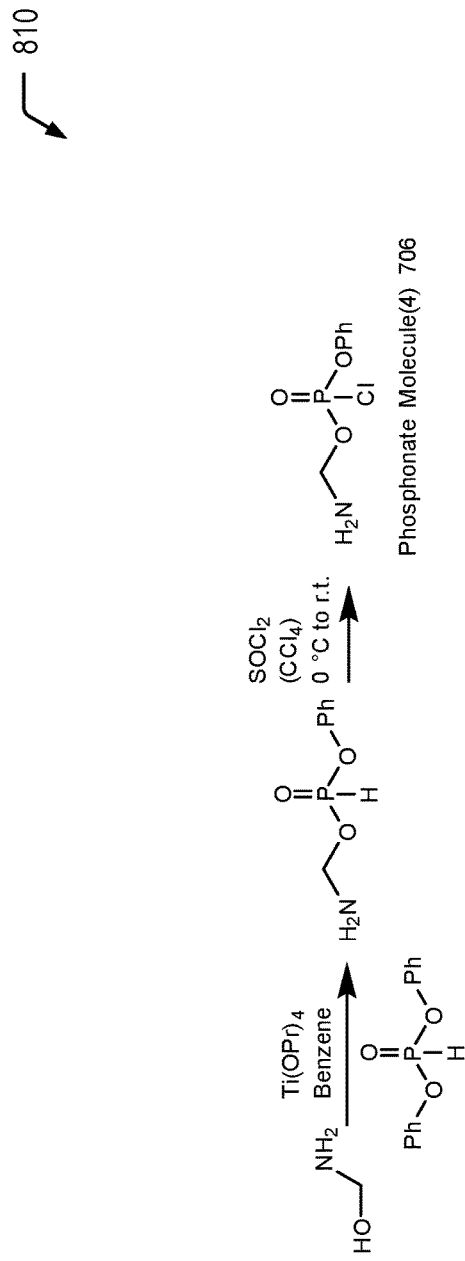

FIGS. 8A and 8B are chemical reaction diagrams showing alternative embodiments of processes of forming the fourth phosphonate molecule 706 depicted in FIG. 7. The fourth phosphonate molecule 706 depicted in FIGS. 8A and 8B represents an example of a phosphonate molecule that is functionalized with a chloride group for bonding with a hydroxyl group of a resveratrol molecule and an amine functional group that may be utilized to form a resveratrol-based flame retardant polymer, as described further herein with respect to FIG. 11.

Referring to FIG. 8A, a first chemical reaction diagram 800 illustrates a first embodiment of a process of forming the fourth phosphonate molecule 706. In FIG. 8A, the fourth phosphonate molecule 706 is formed via a one-step process via reaction of aminomethanol with phenyl dichlorophosphate via careful addition and stoichiometric control.

As a prophetic example, to a stirred solution that includes aminomethanol (1.0 eq.) and triethylamine (2.0 eq.) in anhydrous THF, phenyl dichlorophosphate (1.3 eq.) may be added dropwise at 0° C., and the reaction mixture may be stirred at ambient temperature for 2 hours or the reaction mixture may be heated up to reflux (60-65° C.) for an extended reaction time (4 hours). The reaction mixture may be cooled to ambient temperature and filtered to remove the triethylamine hydrochloride salt. The solvents of the filtrate may be removed in vacuo, and the product may be purified by fractional distillation.

Referring to FIG. 8B, a second chemical reaction diagram 810 illustrates an alternative embodiment of a process of forming the fourth phosphonate molecule 706. The first chemical reaction depicted in FIG. 8B illustrates that aminomethanol may be reacted with titanium (IV) isopropoxide and phosphonic acid diphenyl ester via a pseudo-esterification to form an intermediate molecule. The second chemical reaction depicted in FIG. 8B illustrates that the intermediate molecule may be reacted with thionyl chloride to form the fourth phosphonate molecule 706.

As a prophetic example, diaryl phosphite (5.5 mmol) may be added to a solution of titanium (IV) isopropoxide, $Ti(OPr)_4$ (11 mmol), in aminomethanol (excess). This solution may be diluted with benzene. The reaction mixture may be heated to 40° C. until completion. The mixture may be poured into water, extracted with $CH_2C_{12}$ (3x), dried over $MgSO_4$, and solvent and volatile components may be removed in vacuo. The products may be purified by fractional distillation or recrystallization. The product from the first step (1.0 eq.), in dry acetonitrile (MeCN), toluene, or dichloromethane (DCM), may be added to a solution of trichloroisocyanuric acid (0.33 eq.), N-chlorosuccinimide (1.0 eq.), or tert-butyl hypochlorite (1.0 eq.) in the same solvent at room temperature, under an $N_2$ atmosphere. Upon formation of a precipitate, the reaction may be stirred at room temperature for an additional 2 hours. Upon completion of the reaction, as determined by $^{31}$P NMR, the reaction mixture may be passed through a 0.45 μm Whatman syringe filter and concentrated under vacuum. Next, thionyl chloride (SOCl$_2$) may be dissolved in a suitable solvent, such as carbon tetrachloride (CCl$_4$), and the chemical reaction may be performed from 0° C. to room temperature.

Thus, FIGS. 8A and 8B illustrate alternative processes of forming a phosphonate molecule that is functionalized with a chloride group for bonding with a hydroxyl group of a resveratrol molecule and an amine functional group that may be utilized to form a resveratrol-based flame retardant polymer. While FIGS. 8A and 8B illustrate an example in which the phosphonate molecule includes a phenyl group, it will be appreciated that the phenyl group may be substituted by ethyl, methyl, propyl, or isopropyl groups, among other alternatives.

Figure 9:
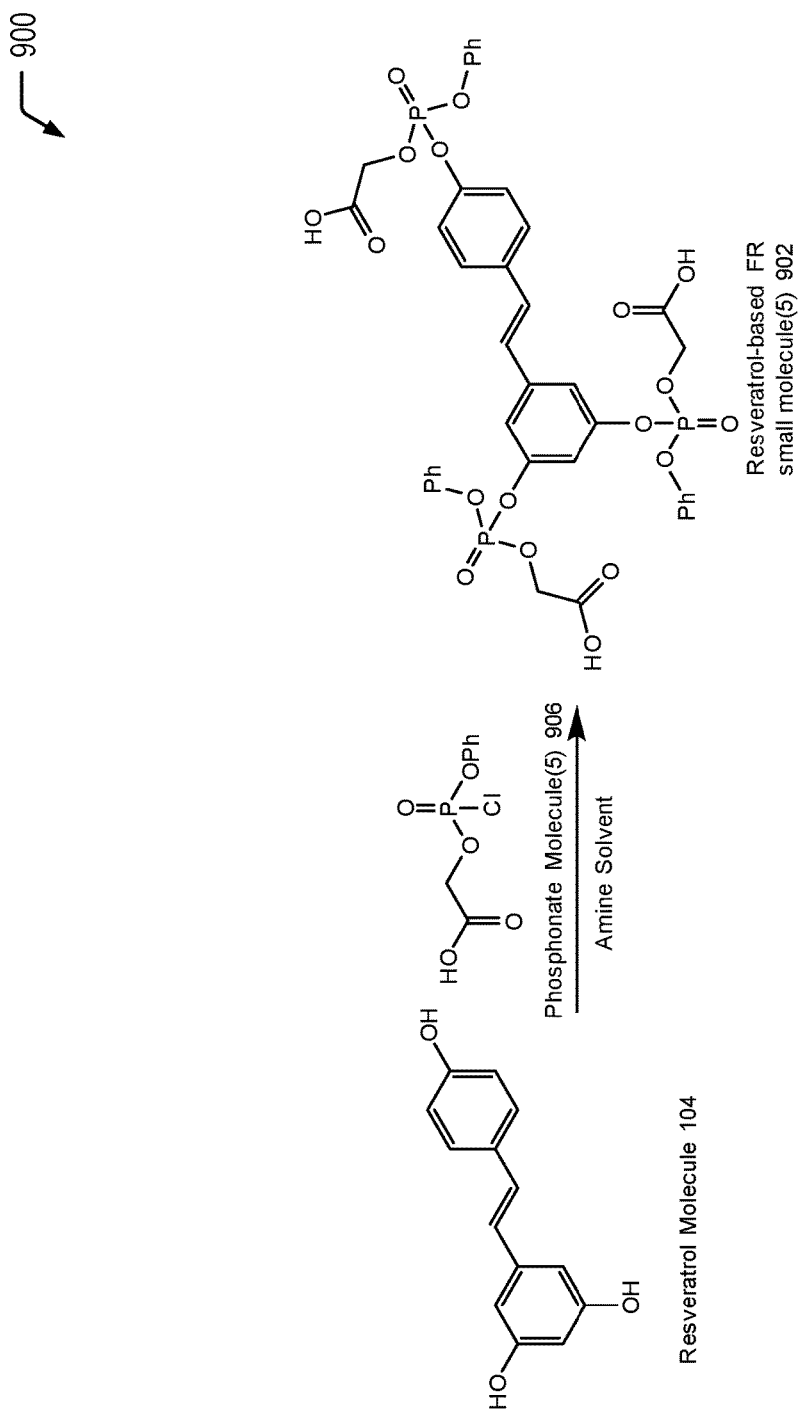
FIG. 9 is a chemical reaction diagram illustrating a process of forming a fifth resveratrol-based flame retardant small molecule, according to one embodiment.

Referring to FIG. 9, a chemical reaction diagram 900 illustrates a process of forming a fifth resveratrol-based FR small molecule 902, according to one embodiment. In the particular embodiment depicted in FIG. 9, the fifth resveratrol-based FR small molecule 902 is formed via a chemical reaction of the resveratrol molecule 104 and a fifth phosphonate molecule 906. As further described herein, the fifth phosphonate molecule 906 depicted in FIG. 9 may be synthesized according to one of the processes described herein with respect to FIGS. 10A and 10B.

The fifth phosphonate molecule 906 depicted in FIG. 9 represents an example of a phosphorus-containing molecule in which the additional reactive group corresponds to a carboxyl group. FIG. 9 illustrates that a chloride group of the fifth phosphonate molecule 906 reacts with a hydroxyl group of the resveratrol molecule 104 to form a phosphorus-oxygen single bond between the phosphorus atom of the phosphoryl group and the oxygen atom of the hydroxyl group. As a prophetic example, the resveratrol molecule 104 may be chemically reacted with the fifth phosphonate molecule 906 in an amine solvent to yield the fifth resveratrol-based FR small molecule 902.

In the embodiment depicted in FIG. 9, each hydroxyl group of the three hydroxyl groups of the resveratrol molecule 104 chemically reacts with the chloride group of the fifth phosphonate molecule 906 to form the fifth resveratrol-based FR small molecule 902 having three phosphorus-based flame retardant moieties (and three carboxyl functional groups). It will be appreciated that, in other cases, the reaction stoichiometry may be adjusted to form an alternative resveratrol-based FR small molecule having less than three phosphorus-based flame retardant moieties (and less than three carboxyl functional groups).

Thus, FIG. 9 illustrates an example of a process of forming a resveratrol-based flame retardant small molecule that includes a carboxyl functional group via a chemical reaction of a resveratrol molecule and a phosphonate molecule that includes the carboxyl functional group.

Figure 10A:
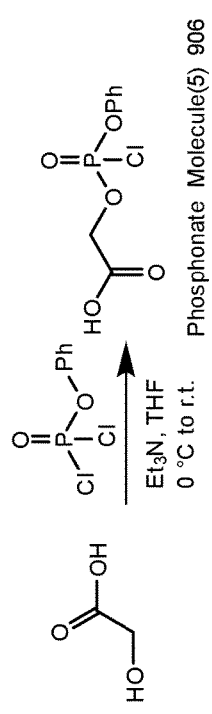
FIGS. 10A and 10B are chemical reaction diagrams showing alternative embodiments of processes of forming a fifth phosphonate molecule for forming the fifth resveratrol-based flame retardant small molecule depicted in FIG. 9.
Figure 10B:
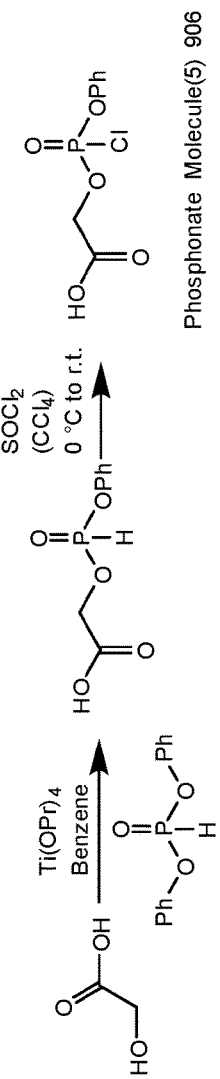

FIGS. 10A and 10B are chemical reaction diagrams showing alternative embodiments of processes of forming the fifth phosphonate molecule 906 depicted in FIG. 9. The fifth phosphonate molecule 906 depicted in FIGS. 10A and 10B represents an example of a phosphonate molecule that is functionalized with a chloride group for bonding with a hydroxyl group of a resveratrol molecule and a carboxyl functional group that may be utilized to form a resveratrol-based flame retardant polymer, as described further herein with respect to FIG. 11.

Referring to FIG. 10A, a first chemical reaction diagram 1000 illustrates a first embodiment of a process of forming the fifth phosphonate molecule 906. In FIG. 10A, the fifth phosphonate molecule 906 is formed via a one-step process via reaction of an α-hydroxy acid (e.g., glycolic acid) with phenyl dichlorophosphate via careful addition and stoichiometric control.

As a prophetic example, to a stirred solution that includes glycolic acid (1.0 eq.) and triethylamine (2.0 eq.) in anhydrous THF, phenyl dichlorophosphate (1.3 eq.) may be added dropwise at 0° C., and the reaction mixture may be stirred at ambient temperature for 2 hours or the reaction mixture may be heated up to reflux (60-65° C.) for an extended reaction time (4 hours). The reaction mixture may be cooled to ambient temperature and filtered to remove the triethylamine hydrochloride salt. The solvents of the filtrate may be removed in vacuo, and the product may be purified by fractional distillation.

Referring to FIG. 10B, a second chemical reaction diagram 1010 illustrates an alternative embodiment of a process of forming the fifth phosphonate molecule 906. The first chemical reaction depicted in FIG. 10B illustrates that an α-hydroxy acid (e.g., glycolic acid) may be reacted with titanium (IV) isopropoxide and phosphonic acid diphenyl ester via a pseudo-esterification to form an intermediate molecule. The second chemical reaction depicted in FIG. 10B illustrates that the intermediate molecule may be reacted with thionyl chloride to form the fifth phosphorus-based FR molecule.

As a prophetic example, diaryl phosphite (5.5 mmol) may be added to a solution of titanium (IV) isopropoxide, Ti(OPr)$_4$ (11 mmol), in glycolic acid (excess). This solution may be diluted with benzene. The reaction mixture may be heated to 40° C. until completion. The mixture may be poured into water, extracted with CH$_2$Cl$_2$ (3×), dried over MgSO$_4$, and solvent and volatile components may be removed in vacuo. The products may be purified by fractional distillation or recrystallization. The product from the first step (1.0 eq.), in dry acetonitrile (MeCN), toluene, or dichloromethane (DCM), may be added to a solution of trichloroisocyanuric acid (0.33 eq.), N-chlorosuccinimide (1.0 eq.), or tert-butyl hypochlorite (1.0 eq.) in the same solvent at room temperature, under an N$_2$ atmosphere. Upon formation of a precipitate, the reaction may be stirred at room temperature for an additional 2 hours. Upon completion of the reaction, as determined by $^{31}$P NMR, the reaction mixture may be passed through a 0.45 μm Whatman syringe filter and concentrated under vacuum. Next, thionyl chloride (SOCl$_2$) may be dissolved in a suitable solvent, such as carbon tetrachloride (CCl$_4$), and the chemical reaction may be performed from 0° C. to room temperature.

Thus, FIGS. 10A and 10B illustrate alternative processes of forming a phosphonate molecule that is functionalized with a chloride group for bonding with a hydroxyl group of a resveratrol molecule and a carboxyl functional group that may be utilized to form a resveratrol-derived flame retardant polymer. While FIGS. 10A and 10B illustrate an example in which the phosphonate molecule includes a phenyl group, it will be appreciated that the phenyl group may be substituted by ethyl, methyl, propyl, or isopropyl groups, among other alternatives.

Figure 11:
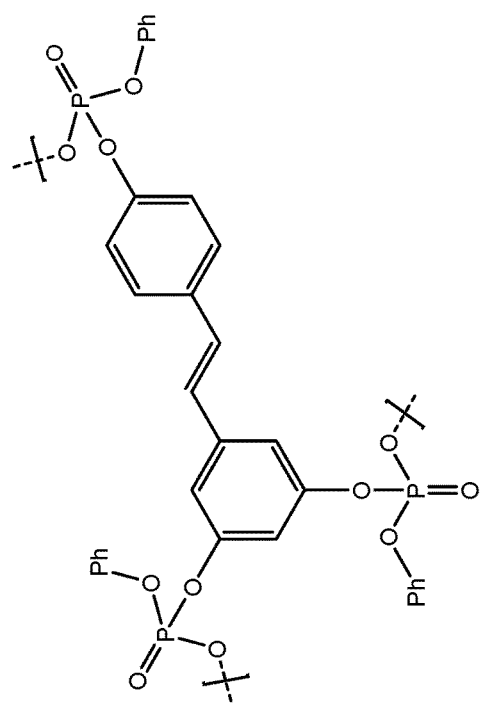
FIG. 11 is a diagram illustrating an example of a resveratrol-based flame retardant polymer formed from one of the resveratrol-based flame retardant small molecules depicted in FIGS. 1, 3, 5, 7, and 9.

Referring to FIG. 11, a diagram 1100 illustrates a first example of a resveratrol-based flame retardant polymer 1102 that may be formed from one of the resveratrol-based flame retardant small molecules depicted in FIGS. 1, 3, 5, 7, and 9.

Figure 12:
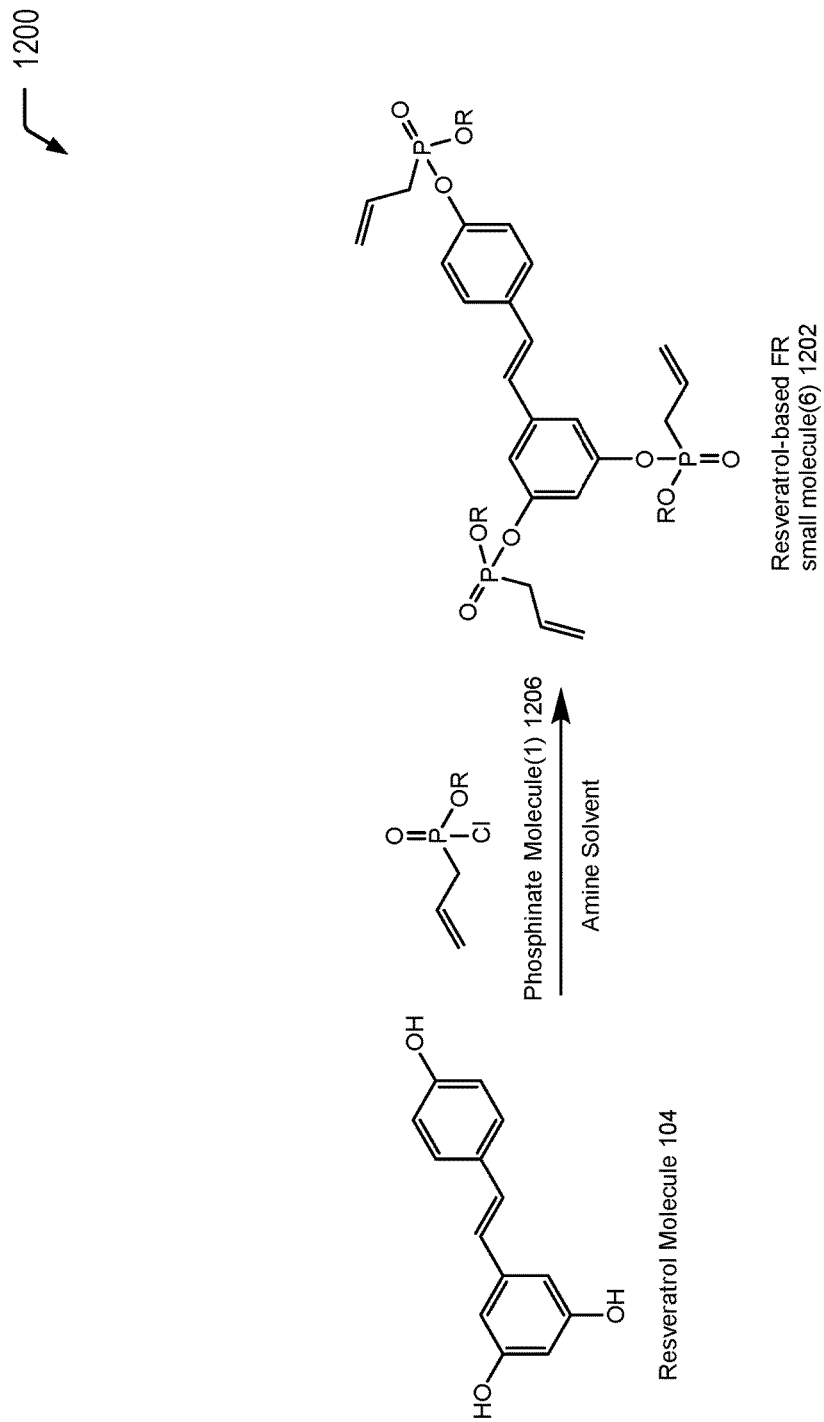
FIG. 12 is a chemical reaction diagram illustrating a process of forming a sixth resveratrol-based flame retardant small molecule, according to one embodiment.

Referring to FIG. 12, a chemical reaction diagram 1200 illustrates a process of forming a sixth resveratrol-based FR small molecule 1202, according to one embodiment. In the particular embodiment depicted in FIG. 12, the sixth resveratrol-based FR small molecule 1202 is formed via a chemical reaction of the resveratrol molecule 104 and a first phosphinate molecule 1206. As further described herein, the first phosphinate molecule 1206 depicted in FIG. 12 may be synthesized according to one of the processes described herein with respect to FIGS. 13A and 13B.

The first phosphinate molecule 1206 depicted in FIG. 12 represents an example of a phosphorus-containing molecule in which the additional reactive group corresponds to an allyl group. FIG. 12 illustrates that a chloride group of the first phosphinate molecule 1206 reacts with a hydroxyl group of the resveratrol molecule 104 to form a phosphorus-oxygen single bond between the phosphorus atom of the phosphoryl group and the oxygen atom of the hydroxyl group. As a prophetic example, the resveratrol molecule 104 may be chemically reacted with the first phosphinate molecule 1206 in an amine solvent to yield the sixth resveratrol-based FR small molecule 1202.

In the embodiment depicted in FIG. 12, each hydroxyl group of the three hydroxyl groups of the resveratrol molecule 104 chemically reacts with the chloride group of the first phosphinate molecule 1206 to form the sixth resveratrol-based FR small molecule 1202 having three phosphorus-based flame retardant moieties (and three allyl functional groups). It will be appreciated that, in other cases, the reaction stoichiometry may be adjusted to form an alternative resveratrol-based FR small molecule having less than three phosphorus-based flame retardant moieties (and less than three allyl functional groups).

Thus, FIG. 12 illustrates an example of a process of forming a resveratrol-based flame retardant small molecule that includes an allyl functional group via a chemical reaction of a resveratrol molecule and a phosphinate molecule that includes the allyl functional group.

Figure 13A:
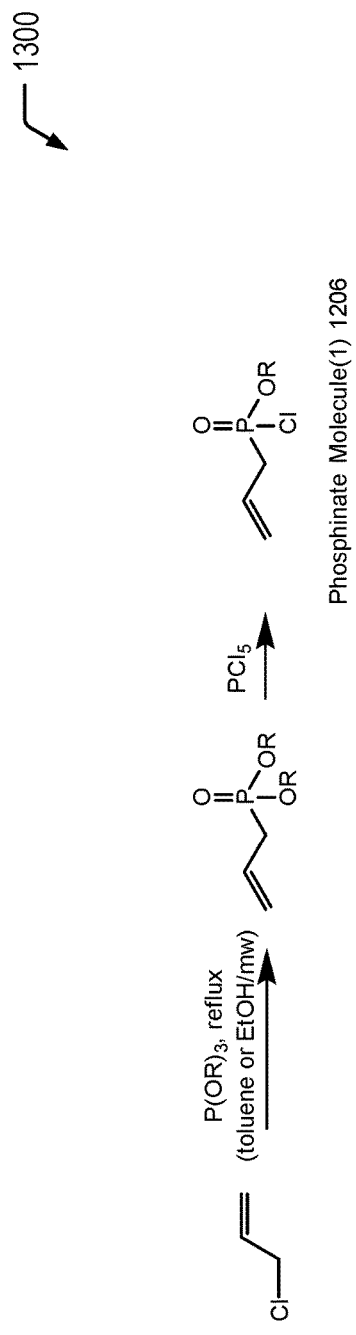
FIGS. 13A and 13B are chemical reaction diagrams showing alternative embodiments of processes of forming a first phosphinate molecule for forming for forming the sixth resveratrol-based flame retardant small molecule depicted in FIG. 11.
Figure 13B:
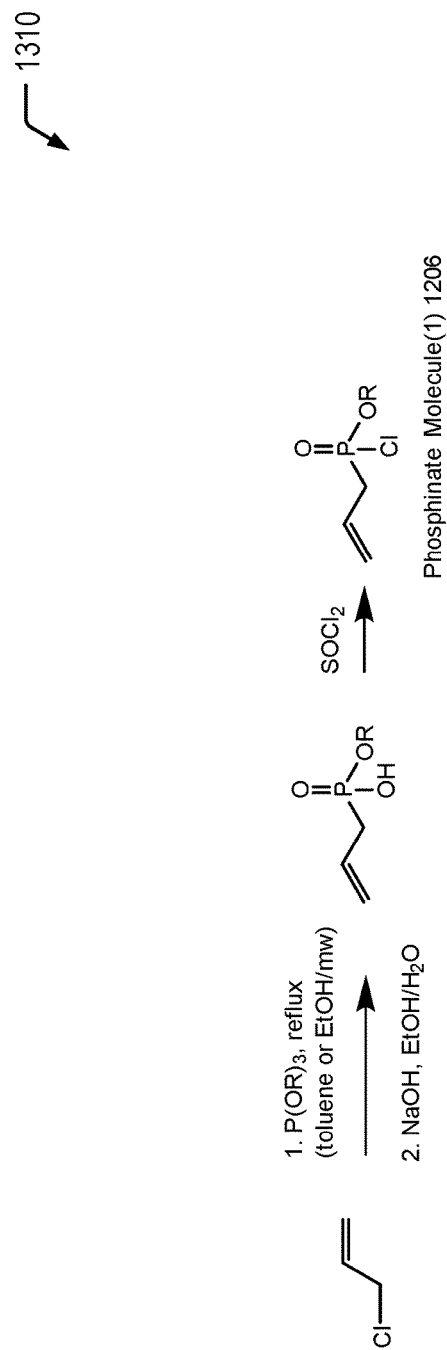

FIGS. 13A and 13B are chemical reaction diagrams showing alternative embodiments of processes of forming the first phosphinate molecule 1206 depicted in FIG. 12. The first phosphinate molecule 1206 depicted in FIGS. 13A and 13B represents an example of a phosphinate molecule that is functionalized with a chloride group for bonding with a hydroxyl group of a resveratrol molecule and an allyl functional group that may be utilized to form a resveratrol-based flame retardant polymer, as described further herein with respect to FIG. 22.

Referring to FIG. 13A, a first chemical reaction diagram 1300 illustrates a first embodiment of a process of forming the first phosphinate molecule 1206. In the first chemical reaction depicted in FIG. 13A, an allyl chloride molecule is chemically reacted with triphenylphosphite to form a phosphonyl ester intermediate material. In the second chemical reaction depicted in FIG. 13A, the phosphonyl ester intermediate material is chemically reacted with phosphorus pentachloride to form the first phosphinate molecule 1206.

As a prophetic example, allyl chloride (1 eq.) and trialkyl phosphite, P(OR)$_3$, may be added to a reaction vessel. The reaction vessel may include an organic solvent such as toluene, THF, ethanol, or DMF, and may also contain a compound such an alumina. The reaction may be heated to reflux or up to 180° C. if done using neat conditions. The reaction mixture may also be irradiated by microwaves for a short period to increase the reaction rate. The reaction may be cooled to room temperature, and the excess trialkyl phosphite may be removed in vacuo or it may be washed with DCM, and dried using CaCl$_2$ prior to filtration and having the solvents removed in vacuo. The phosphonate may be purified by fractional distillation. To a solution of the phosphonate product may be added PCl$_5$ (excess) at 0° C. under an inert atmosphere. The reaction may be performed in a solvent such as CCl$_4$. The mixture may be allowed to warm up to room temperature and may be stirred for an additional day. The solvent may then be removed in vacuo, and the residue may be distilled to give the product.

Referring to FIG. 13B, a second chemical reaction diagram 1310 illustrates an alternative embodiment of a process of forming the first phosphinate molecule 1206. In the first chemical reaction depicted in FIG. 13B, an allyl chloride molecule is chemically reacted with triphenylphosphite and quenched under aqueous basic conditions to form a phosphonyl ester intermediate material. In the second chemical reaction depicted in FIG. 13B, the phosphonyl ester intermediate material is chemically reacted with thionyl chloride to form the first phosphinate molecule 1206.

As a prophetic example, an allyl phosphonate (1.0 eq.) may be generated and quickly added to a solution of bromodimethyl borane (1.0 eq.) in an organic solvent such as toluene. The reaction mixture may be warmed to room temperature and stirred overnight. The solvent and volatile byproducts may be removed in vacuo. To a solution of the diaryl phosphorous-containing product, SOCl$_2$ (excess) may be added at 0° C. The mixture may be allowed to warm up to room temperature or heated to 40° C. and may be stirred for an additional day. The solvent may then be removed in vacuo, and the residue may be distilled to give the product.

Thus, FIGS. 13A and 13B illustrate alternative processes of forming a phosphinate molecule that is functionalized with a chloride group for bonding with a hydroxyl group of a resveratrol molecule and an allyl functional group that may be utilized to form a resveratrol-based flame retardant polymer. While FIGS. 13A and 13B illustrate an example in which the phosphinate molecule includes a phenyl group, it will be appreciated that the phenyl group may be substituted by ethyl, methyl, propyl, or isopropyl groups, among other alternatives.

Figure 14:
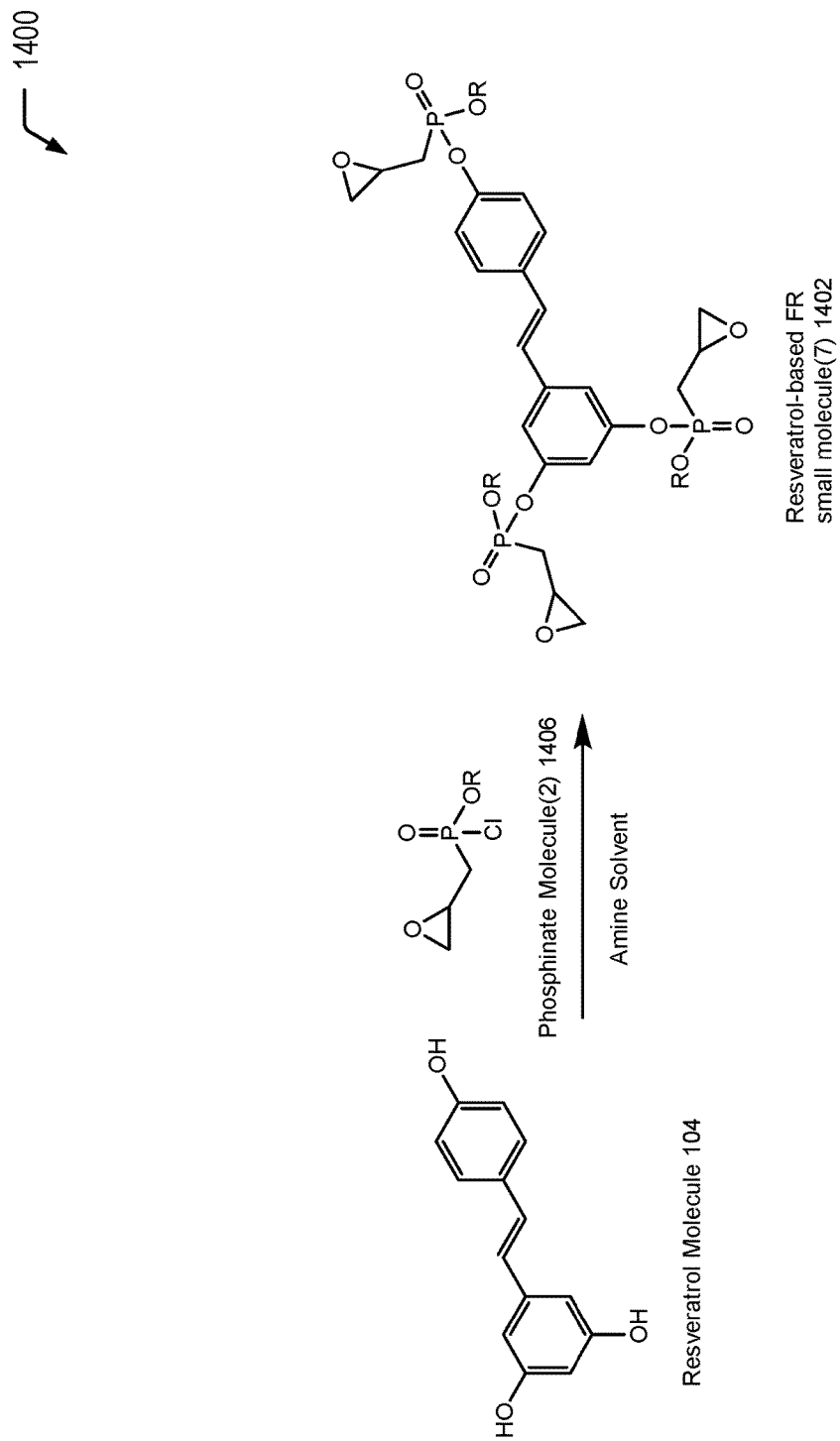
FIG. 14 is a chemical reaction diagram illustrating a process of forming a seventh resveratrol-based flame retardant small molecule, according to one embodiment.

Referring to FIG. 14, a chemical reaction diagram 1400 illustrates a process of forming a seventh resveratrol-based FR small molecule 1402, according to one embodiment. In the particular embodiment depicted in FIG. 14, the seventh resveratrol-based FR small molecule 1402 is formed via a chemical reaction of the resveratrol molecule 104 and a second phosphinate molecule 1406. As further described herein, the second phosphinate molecule 1406 depicted in FIG. 14 may be synthesized according to one of the processes described herein with respect to FIGS. 15A and 15B.

The second phosphinate molecule 1406 depicted in FIG. 14 represents an example of a phosphorus-containing molecule in which the additional reactive group corresponds to an epoxide group. FIG. 14 illustrates that a chloride group of the second phosphinate molecule 1406 reacts with a hydroxyl group of the resveratrol molecule 104 to form a phosphorus-oxygen single bond between the phosphorus atom of the phosphoryl group and the oxygen atom of the hydroxyl group. As a prophetic example, the resveratrol molecule 104 may be chemically reacted with the second phosphinate molecule 1406 in an amine solvent to yield the seventh resveratrol-based FR small molecule 1402.

In the embodiment depicted in FIG. 14, each hydroxyl group of the three hydroxyl groups of the resveratrol molecule 104 chemically reacts with the chloride group of the second phosphinate molecule 1406 to form the seventh resveratrol-based FR small molecule 1402 having three phosphorus-based flame retardant moieties (and three epoxide functional groups). It will be appreciated that, in other cases, the reaction stoichiometry may be adjusted to form an alternative FR small molecule having less than three phosphorus-based flame retardant moieties (and less than three epoxide functional groups).

Thus, FIG. 14 illustrates an example of a process of forming a resveratrol-derived flame retardant small molecule that includes an epoxide functional group via a chemical reaction of a resveratrol molecule and a phosphinate molecule that includes the epoxide functional group.

Figure 15A:
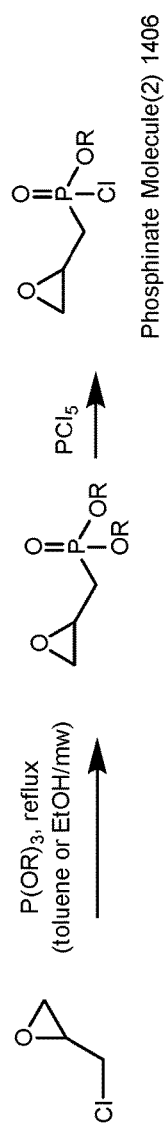
FIGS. 15A and 15B are chemical reaction diagrams showing alternative embodiments of processes of forming a second phosphinate molecule for forming the seventh resveratrol-based flame retardant small molecule depicted in FIG. 14.
Figure 15B:
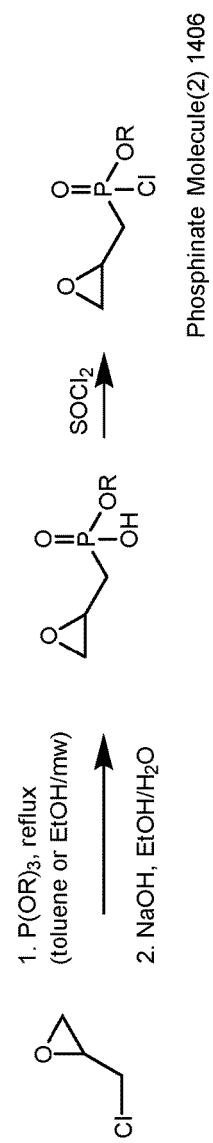

FIGS. 15A and 15B are chemical reaction diagrams showing alternative embodiments of processes of forming the second phosphinate molecule 1406 depicted in FIG. 14. The second phosphinate molecule 1406 depicted in FIGS. 15A and 15B represents an example of a phosphinate molecule that is functionalized with a chloride group for bonding with a hydroxyl group of a resveratrol molecule and an epoxide functional group that may be utilized to form a resveratrol-based flame retardant polymer, as described further herein with respect to FIG. 22.

Referring to FIG. 15A, a first chemical reaction diagram 1500 illustrates a first embodiment of a process of forming the second phosphinate molecule 1406. In the first chemical reaction depicted in FIG. 15A, an epichlorohydrin molecule is chemically reacted with triphenylphosphite to form a phosphonyl ester intermediate material. In the second chemical reaction depicted in FIG. 15A, the phosphonyl ester intermediate material is chemically reacted with phosphorus pentachloride to form the second phosphinate molecule 1406.

As a prophetic example, epichlorohydrin (1 eq.) and trialkyl phosphite, $P(OR)_3$, may be added to a reaction vessel. The reaction vessel may include an organic solvent such as toluene, THF, ethanol, or DMF, and may also contain a compound such an alumina. The reaction may be heated to reflux or up to 180° C. if done using neat conditions. The reaction mixture may also be irradiated by microwaves for a short period to increase the reaction rate. The reaction may be cooled to room temperature, and the excess trialkyl phosphite may be removed in vacuo or it may be washed with DCM, and dried using $CaCl_2$ prior to filtration and having the solvents removed in vacuo. The phosphonate may be purified by fractional distillation. To a solution of the phosphonate product may be added $PCl_5$ (excess) at 0° C. under an inert atmosphere. The reaction may be performed in a solvent such as $CCl_4$. The mixture may be allowed to warm up to room temperature and may be stirred for an additional day. The solvent may then be removed in vacuo, and the residue may be distilled to give the product.

Referring to FIG. 15B, a second chemical reaction diagram 1510 illustrates an alternative embodiment of a process of forming the second phosphinate molecule 1406. In the first chemical reaction depicted in FIG. 15B, an epichlorohydrin molecule is chemically reacted with triphenylphosphite and quenched under aqueous basic conditions to form a phosphonyl ester intermediate material. In the second chemical reaction depicted in FIG. 15B, the phosphonyl ester intermediate material is chemically reacted with thionyl chloride to form the second phosphinate molecule 1406.

As a prophetic example, an oxirane phosphonate (1.0 eq.) may be generated and quickly added to a solution of bromodimethyl borane (1.0 eq.) in an organic solvent such as toluene. The reaction mixture may be warmed to room temperature and stirred overnight. The solvent and volatile byproducts may be removed in vacuo. To a solution of the diaryl phosphorous-containing product, $SOCl_2$ (excess) may be added at 0° C. The mixture may be allowed to warm up to room temperature or heated to 40° C. and may be stirred for an additional day. The solvent may then be removed in vacuo, and the residue may be distilled to give the product.

Thus, FIGS. 15A and 15B illustrate alternative processes of forming a phosphinate molecule that is functionalized with a chloride group for bonding with a hydroxyl group of a resveratrol molecule and an epoxide functional group that may be utilized to form a resveratrol-based flame retardant polymer. While FIGS. 15A and 15B illustrate an example in which the phosphinate molecule includes a phenyl group, it will be appreciated that the phenyl group may be substituted by ethyl, methyl, propyl, or isopropyl groups, among other alternatives.

Referring to FIG. 16, a chemical reaction diagram 1600 illustrates a process of forming an eighth resveratrol-based FR small molecule 1602, according to one embodiment. In the particular embodiment depicted in FIG. 16, the eighth resveratrol-based FR small molecule 1602 is formed via a chemical reaction of the resveratrol molecule 104 and a third phosphinate molecule 1606. As further described herein, the third phosphinate molecule 1606 depicted in FIG. 16 may be synthesized according to one of the processes described herein with respect to FIGS. 17A and 17B.

The third phosphinate molecule 1606 depicted in FIG. 16 represents an example of a phosphorus-containing molecule in which the additional reactive group corresponds to a lactone group. FIG. 16 illustrates that a chloride group of the third phosphinate molecule 1606 reacts with a hydroxyl group of the resveratrol molecule 104 to form a phosphorus-oxygen single bond between the phosphorus atom of the phosphoryl group and the oxygen atom of the hydroxyl group. As a prophetic example, the resveratrol molecule 104 may be chemically reacted with the third phosphinate molecule 1606 in an amine solvent to yield the eighth resveratrol-based FR small molecule 1602.

In the embodiment depicted in FIG. 16, each hydroxyl group of the three hydroxyl groups of the resveratrol molecule 104 chemically reacts with the chloride group of the third phosphinate molecule 1606 to form the eighth resveratrol-based FR small molecule 1602 having three phosphorus-based flame retardant moieties (and three lactone functional groups). It will be appreciated that, in other cases, the reaction stoichiometry may be adjusted to form an alternative resveratrol-based FR small molecule having less than three phosphorus-based flame retardant moieties (and less than three lactone functional groups).

Thus, FIG. 16 illustrates an example of a process of forming a resveratrol-based flame retardant small molecule that includes a lactone functional group via a chemical reaction of a resveratrol molecule and a phosphinate molecule that includes the lactone functional group.

Figure 17A:
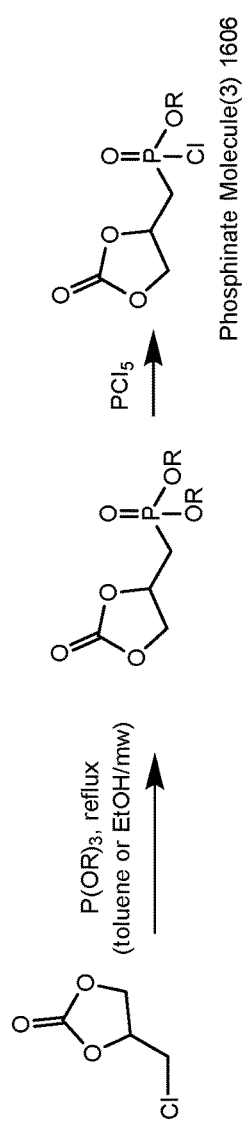
FIGS. 17A and 17B are chemical reaction diagrams showing alternative embodiments of processes of forming a third phosphinate molecule for forming the eighth resveratrol-based flame retardant small molecule depicted in FIG. 16.
Figure 17B:
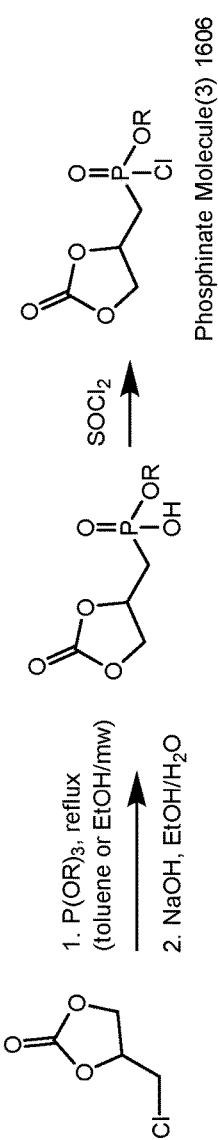

FIGS. 17A and 17B are chemical reaction diagrams showing alternative embodiments of processes of forming the third phosphinate molecule 1606 depicted in FIG. 16. The third phosphinate molecule 1606 depicted in FIGS. 17A and 17B represents an example of a phosphinate molecule that is functionalized with a chloride group for bonding with a hydroxyl group of a resveratrol molecule and a lactone functional group that may be utilized to form a resveratrol-based flame retardant polymer, as described further herein with respect to FIG. 22.

Referring to FIG. 17A, a first chemical reaction diagram 1700 illustrates a first embodiment of a process of forming the third phosphinate molecule 1606. In the first chemical reaction depicted in FIG. 17A, a (chloromethyl)ethylene carbonate molecule is chemically reacted with triphenylphosphite to form a phosphonyl ester intermediate material. In the second chemical reaction depicted in FIG. 17A, the phosphonyl ester intermediate material is chemically reacted with phosphorus pentachloride to form the third phosphinate molecule 1606.

As a prophetic example, (chloromethyl)ethylene carbonate (1 eq.) and trialkyl phosphite, P(OR)$_3$, may be added to a reaction vessel. The reaction vessel may include an organic solvent such as toluene, THF, ethanol, or DMF, and may also contain a compound such an alumina. The reaction may be heated to reflux or up to 180° C. if done using neat conditions. The reaction mixture may also be irradiated by microwaves for a short period to increase the reaction rate. The reaction may be cooled to room temperature, and the excess trialkyl phosphite may be removed in vacuo or it may be washed with DCM, and dried using CaCl$_2$ prior to filtration and having the solvents removed in vacuo. The phosphonate may be purified by fractional distillation. To a solution of the phosphonate product may be added PCl$_5$ (excess) at 0° C. under an inert atmosphere. The reaction may be performed in a solvent such as CCl$_4$. The mixture may be allowed to warm up to room temperature and may be stirred for an additional day. The solvent may then be removed in vacuo, and the residue may be distilled to give the product.

Referring to FIG. 17B, a second chemical reaction diagram 1710 illustrates an alternative embodiment of a process of forming the third phosphinate molecule 1606. In the first chemical reaction depicted in FIG. 17B, a (chloromethyl) ethylene carbonate molecule is chemically reacted with triphenylphosphite and quenched under aqueous basic conditions to form a phosphonyl ester intermediate material. In the second chemical reaction depicted in FIG. 17B, the phosphonyl ester intermediate material is chemically reacted with thionyl chloride to form the third phosphinate molecule 1606.

As a prophetic example, a lactone phosphonate (1.0 eq.) may be generated and quickly added to a solution of bromodimethyl borane (1.0 eq.) in an organic solvent such as toluene. The reaction mixture may be warmed to room temperature and stirred overnight. The solvent and volatile byproducts may be removed in vacuo. To a solution of the diaryl phosphorous-containing product, SOCl$_2$ (excess) may be added at 0° C. The mixture may be allowed to warm up to room temperature or heated to 40° C. and may be stirred for an additional day. The solvent may then be removed in vacuo, and the residue may be distilled to give the product.

Thus, FIGS. 17A and 17B illustrate alternative processes of forming a phosphinate molecule that is functionalized with a chloride group for bonding with a hydroxyl group of a resveratrol molecule and a lactone functional group that may be utilized to form a resveratrol-based flame retardant polymer. While FIGS. 17A and 17B illustrate an example in which the phosphinate molecule includes a phenyl group, it will be appreciated that the phenyl group may be substituted by ethyl, methyl, propyl, or isopropyl groups, among other alternatives.

Figure 18:
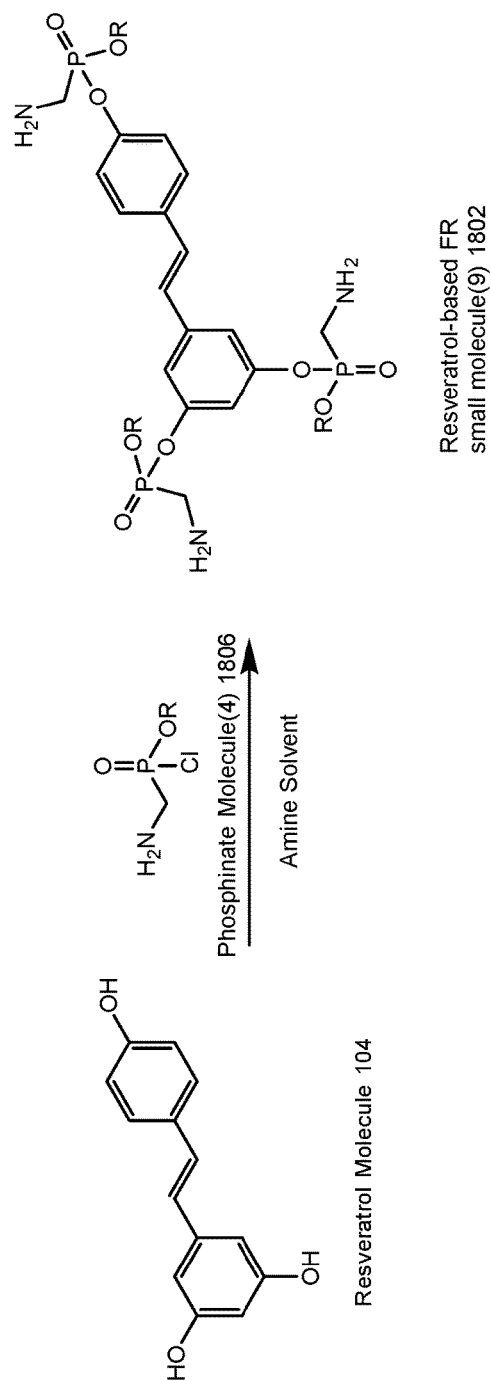
FIG. 18 is a chemical reaction diagram illustrating a process of forming a ninth resveratrol-based flame retardant small molecule, according to one embodiment.

Referring to FIG. 18, a chemical reaction diagram 1800 illustrates a process of forming a ninth resveratrol-based FR small molecule 1802, according to one embodiment. In the particular embodiment depicted in FIG. 18, the ninth resveratrol-based FR small molecule 1802 is formed via a chemical reaction of the resveratrol molecule 104 and a fourth phosphinate molecule 1806. As further described herein, the fourth phosphinate molecule 1806 depicted in FIG. 18 may be synthesized according to one of the processes described herein with respect to FIGS. 19A and 19B.

The fourth phosphinate molecule 1806 depicted in FIG. 18 represents an example of a phosphorus-containing molecule in which the additional reactive group corresponds to an amine group. FIG. 18 illustrates that a chloride group of the fourth phosphinate molecule 1806 reacts with a hydroxyl group of the resveratrol molecule 104 to form a phosphorus-oxygen single bond between the phosphorus atom of the phosphoryl group and the oxygen atom of the hydroxyl group. As a prophetic example, the resveratrol molecule 104 may be chemically reacted with the fourth phosphinate molecule 1806 in an amine solvent to yield the ninth resveratrol-based FR small molecule 1802.

In the embodiment depicted in FIG. 18, each hydroxyl group of the three hydroxyl groups of the resveratrol molecule 104 chemically reacts with the chloride group of the fourth phosphinate molecule 1806 to form the ninth resveratrol-based FR small molecule 1802 having three phosphorus-based flame retardant moieties (and three amine functional groups). It will be appreciated that, in other cases, the reaction stoichiometry may be adjusted to form an alternative resveratrol-based FR small molecule having less than three phosphorus-based flame retardant moieties (and less than three amine functional groups).

Thus, FIG. 18 illustrates an example of a process of forming a resveratrol-based flame retardant small molecule that includes an amine functional group via a chemical reaction of a resveratrol molecule and a phosphinate molecule that includes the amine functional group.

FIGS. 19A and 19B are chemical reaction diagrams showing alternative embodiments of processes of forming the fourth phosphinate molecule 1806 depicted in FIG. 18. The fourth phosphinate molecule 1806 depicted in FIGS. 19A and 19B represents an example of a phosphinate molecule that is functionalized with a chloride group for bonding with a hydroxyl group of a resveratrol molecule and an amine functional group that may be utilized to form a resveratrol-based flame retardant polymer, as described further herein with respect to FIG. 22.

Referring to FIG. 19A, a first chemical reaction diagram 1900 illustrates a first embodiment of a process of forming the fourth phosphinate molecule 1806. In the first chemical reaction depicted in FIG. 19A, a chloromethylamine molecule is chemically reacted with triphenylphosphite to form a phosphonyl ester intermediate material. In the second chemical reaction depicted in FIG. 19A, the phosphonyl ester intermediate material is chemically reacted with phosphorus pentachloride to form the fourth phosphinate molecule 1806.

As a prophetic example, chloromethylamine (1 eq.) and trialkyl phosphite, P(OR)$_3$, may be added to a reaction vessel. The reaction vessel may include an organic solvent such as toluene, THF, ethanol, or DMF, and may also contain a compound such an alumina. The reaction may be heated to reflux or up to 180° C. if done using neat conditions. The reaction mixture may also be irradiated by microwaves for a short period to increase the reaction rate. The reaction may be cooled to room temperature, and the excess trialkyl phosphite may be removed in vacuo or it may be washed with DCM, and dried using CaCl$_2$ prior to filtration and having the solvents removed in vacuo. The phosphonate may be purified by fractional distillation. To a solution of the phosphonate product may be added PCl$_5$ (excess) at 0° C. under an inert atmosphere. The reaction may be performed in a solvent such as CCl$_4$. The mixture may be allowed to warm up to room temperature and may be stirred for an additional day. The solvent may then be removed in vacuo, and the residue may be distilled to give the product.

Referring to FIG. 19B, a second chemical reaction diagram 1910 illustrates an alternative embodiment of a process of forming the fourth phosphinate molecule 1806. In the first chemical reaction depicted in FIG. 19B, a chloromethylamine molecule is chemically reacted with triphenylphosphite and quenched under aqueous basic conditions to form a phosphonyl ester intermediate material. In the second chemical reaction depicted in FIG. 19B, the phosphonyl ester intermediate material is chemically reacted with thionyl chloride to form the fourth phosphinate molecule 1806.

As a prophetic example, an amine phosphonate (1.0 eq.) may be generated and quickly added to a solution of bromodimethyl borane (1.0 eq.) in an organic solvent such as toluene. The reaction mixture may be warmed to room temperature and stirred overnight. The solvent and volatile byproducts may be removed in vacuo. To a solution of the diaryl phosphorous-containing product, $SOCl_2$ (excess) may be added at 0° C. The mixture may be allowed to warm up to room temperature or heated to 40° C. and may be stirred for an additional day. The solvent may then be removed in vacuo, and the residue may be distilled to give the product.

Thus, FIGS. 19A and 19B illustrate alternative processes of forming a phosphinate molecule that is functionalized with a chloride group for bonding with a hydroxyl group of a resveratrol molecule and an amine functional group that may be utilized to form a resveratrol-derived flame retardant polymer. While FIGS. 19A and 19B illustrate an example in which the phosphinate molecule includes a phenyl group, it will be appreciated that the phenyl group may be substituted by ethyl, methyl, propyl, or isopropyl groups, among other alternatives.

Referring to FIG. 20, a chemical reaction diagram 2000 illustrates a process of forming a tenth resveratrol-based FR small molecule 2002, according to one embodiment. In the particular embodiment depicted in FIG. 20, the tenth resveratrol-based FR small molecule 2002 is formed via a chemical reaction of the resveratrol molecule 104 and a fifth phosphinate molecule 2006. As further described herein, the fifth phosphinate molecule 2006 depicted in FIG. 20 may be synthesized according to one of the processes described herein with respect to FIGS. 21A and 21B.

The fifth phosphinate molecule 2006 depicted in FIG. 20 represents an example of a phosphorus-containing molecule in which the additional reactive group corresponds to a carboxyl group. FIG. 20 illustrates that a chloride group of the fifth phosphinate molecule 2006 reacts with a hydroxyl group of the resveratrol molecule 104 to form a phosphorus-oxygen single bond between the phosphorus atom of the phosphoryl group and the oxygen atom of the hydroxyl group. As a prophetic example, the resveratrol molecule 104 may be chemically reacted with the fifth phosphinate molecule 2006 in an amine solvent to yield the tenth resveratrol-based FR small molecule 2002.

In the embodiment depicted in FIG. 20, each hydroxyl group of the three hydroxyl groups of the resveratrol molecule 104 chemically reacts with the chloride group of the fifth phosphinate molecule 2006 to form the tenth resveratrol-based FR small molecule 2002 having three phosphorus-based flame retardant moieties (and three carboxyl functional groups). It will be appreciated that, in other cases, the reaction stoichiometry may be adjusted to form an alternative resveratrol-based FR small molecule having less than three phosphorus-based flame retardant moieties (and less than three carboxyl functional groups).

Thus, FIG. 20 illustrates an example of a process of forming a resveratrol-based flame retardant small molecule that includes a carboxyl functional group via a chemical reaction of a resveratrol molecule and a phosphinate molecule that includes the carboxyl functional group.

Figure 21A:
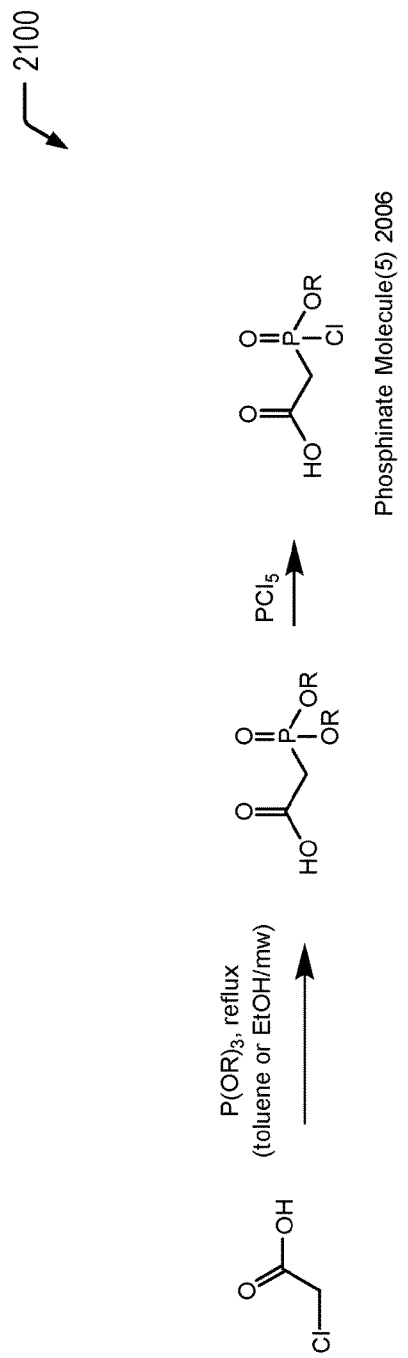
FIGS. 21A and 21B are chemical reaction diagrams showing alternative embodiments of processes of forming a fifth phosphinate molecule for forming the tenth resveratrol-based flame retardant small molecule depicted in FIG. 20.
Figure 21B:
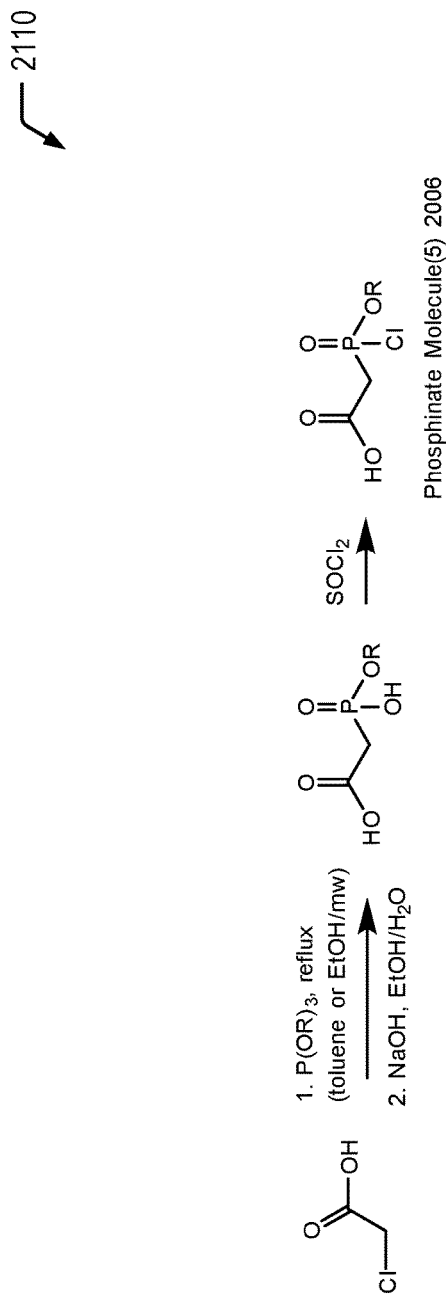

FIGS. 21A and 21B are chemical reaction diagrams showing alternative embodiments of processes of forming the fifth phosphinate molecule 2006 depicted in FIG. 20. The fifth phosphinate molecule 2006 depicted in FIGS. 21A and 21B represents an example of a phosphinate molecule that is functionalized with a chloride group for bonding with a hydroxyl group of a resveratrol molecule and a carboxyl functional group that may be utilized to form a resveratrol-based flame retardant polymer, as described further herein with respect to FIG. 22.

Referring to FIG. 21A, a first chemical reaction diagram 2100 illustrates a first embodiment of a process of forming the fifth phosphinate molecule 2006. In the first chemical reaction depicted in FIG. 21A, a chloroacetic acid molecule is chemically reacted with triphenylphosphite to form a phosphonyl ester intermediate material. In the second chemical reaction depicted in FIG. 21A, the phosphonyl ester intermediate material is chemically reacted with phosphorus pentachloride to form the fifth phosphinate molecule 2006.

As a prophetic example, chloroacetic acid (1 eq.) and trialkyl phosphite, $P(OR)_3$, may be added to a reaction vessel. The reaction vessel may include an organic solvent such as toluene, THF, ethanol, or DMF, and may also contain a compound such an alumina. The reaction may be heated to reflux or up to 180° C. if done using neat conditions. The reaction mixture may also be irradiated by microwaves for a short period to increase the reaction rate. The reaction may be cooled to room temperature, and the excess trialkyl phosphite may be removed in vacuo or it may be washed with DCM, and dried using $CaCl_2$ prior to filtration and having the solvents removed in vacuo. The phosphonate may be purified by fractional distillation. To a solution of the phosphonate product may be added $PCl_5$ (excess) at 0° C. under an inert atmosphere. The reaction may be performed in a solvent such as $CCl_4$. The mixture may be allowed to warm up to room temperature and may be stirred for an additional day. The solvent may then be removed in vacuo, and the residue may be distilled to give the product.

Referring to FIG. 21B, a second chemical reaction diagram 2110 illustrates an alternative embodiment of a process of forming the fifth phosphinate molecule 2006. In the first chemical reaction depicted in FIG. 21B, a chloroacetic acid molecule is chemically reacted with triphenylphosphite and quenched under aqueous basic conditions to form a phosphonyl ester intermediate material. In the second chemical reaction depicted in FIG. 21B, the phosphonyl ester intermediate material is chemically reacted with thionyl chloride to form the fifth phosphinate molecule 2006.

As a prophetic example, a carboxyl phosphonate (1.0 eq.) may be generated and quickly added to a solution of bromodimethyl borane (1.0 eq.) in an organic solvent such as toluene. The reaction mixture may be warmed to room temperature and stirred overnight. The solvent and volatile byproducts may be removed in vacuo. To a solution of the diaryl phosphorous-containing product, $SOCl_2$ (excess) may be added at 0° C. The mixture may be allowed to warm up to room temperature or heated to 40° C. and may be stirred for an additional day. The solvent may then be removed in vacuo, and the residue may be distilled to give the product.

Thus, FIGS. 21A and 21B illustrate alternative processes of forming a phosphinate molecule that is functionalized with a chloride group for bonding with a hydroxyl group of a resveratrol molecule and a carboxyl functional group that may be utilized to form a resveratrol-based flame retardant polymer. While FIGS. 21A and 21B illustrate an example in which the phosphinate molecule includes a phenyl group, it will be appreciated that the phenyl group may be substituted by ethyl, methyl, propyl, or isopropyl groups, among other alternatives.

Figure 22:
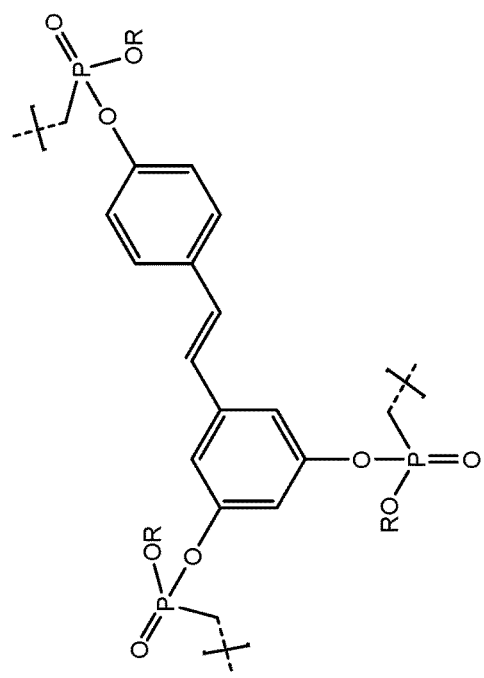
FIG. 22 is a diagram illustrating an example of a resveratrol-based flame retardant polymer formed from one of the resveratrol-based flame retardant small molecules depicted in FIGS. 12, 14, 16, 18, and 20.

Referring to FIG. 22, a diagram 2200 illustrates a second example of a resveratrol-based flame retardant polymer 2202 that may be formed from one of the resveratrol-based flame retardant small molecules depicted in FIGS. 12, 14, 16, 18, and 20.

It will be understood from the foregoing description that modifications and changes may be made in various embodiments of the present invention without departing from its true spirit. The descriptions in this specification are for purposes of illustration only and are not to be construed in a limiting sense. The scope of the present invention is limited only by the language of the following claims.

What is claimed is:

1. A process of forming a resveratrol-based flame retardant polymer, the process comprising:

forming a resveratrol-based flame retardant small molecule via a chemical reaction of a resveratrol molecule with a phosphorus-containing molecule that includes a chloride group and a terminal functional group, the terminal functional group selected from the group consisting of: an allyl group; an epoxide group; a lactone group; an amine group; and a carboxyl group; and utilizing the resveratrol-based flame retardant small molecule to form a resveratrol-based flame retardant polymer via a chemical reaction of the terminal functional group.

2. The process of claim 1, wherein the phosphorus-containing molecule includes a phosphonate molecule.

3. The process of claim 2, wherein the resveratrol-based flame retardant small molecule has the following chemical structure:

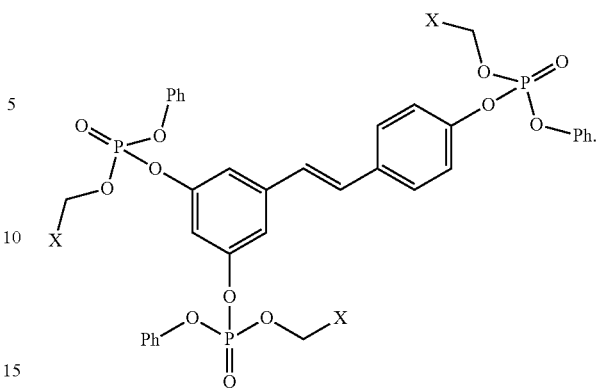

wherein X includes the terminal functional group.

4. The process of claim 1, wherein the phosphorus-containing molecule includes a phosphinate molecule.

5. The process of claim 4, wherein the resveratrol-based flame retardant small molecule has the following chemical structure:

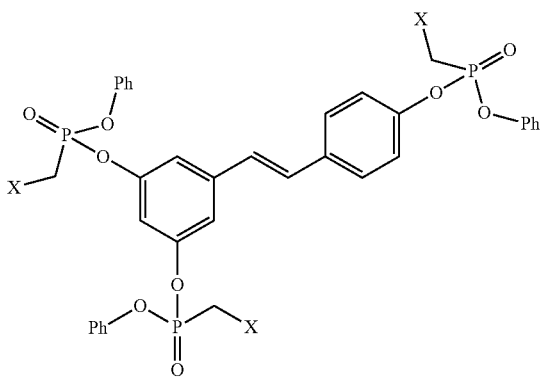

wherein X includes the terminal functional group.

* * * * *